(12) United States Patent
Baruah et al.

(10) Patent No.: US 10,913,801 B2
(45) Date of Patent: Feb. 9, 2021

(54) PD-1 ANTIBODIES

(71) Applicant: INNOVENT BIOLOGICS (SUZHOU) CO., LTD, Suzhou (CN)

(72) Inventors: Hemanta Baruah, Indianapolis, IN (US); Cheng Chen, Suzhou (CN); Xiaolin Liu, Suzhou (CN); Andy Tsun, Suzhou (CN); De-Chao Michael Yu, Suzhou (CN)

(73) Assignee: INNOVENT BIOLOGICS (SUZHOU) CO., LTD., Jiangsu (CN)

( * ) Notice: Subject to any disclaimer, the term of this patent is extended or adjusted under 35 U.S.C. 154(b) by 248 days.

(21) Appl. No.: 16/073,942

(22) PCT Filed: Jan. 23, 2017

(86) PCT No.: PCT/CN2017/072190
§ 371 (c)(1),
(2) Date: Jul. 30, 2018

(87) PCT Pub. No.: WO2017/133540
PCT Pub. Date: Aug. 10, 2017

(65) Prior Publication Data
US 2019/0040149 A1   Feb. 7, 2019

(30) Foreign Application Priority Data
Feb. 2, 2016  (WO) ............... PCT/CN2016/073169

(51) Int. Cl.
| | | |
|---|---|---|
| *C07K 16/28* | (2006.01) |
| *A61P 35/00* | (2006.01) |
| *A61K 39/395* | (2006.01) |
| *C12N 5/10* | (2006.01) |
| *A61K 39/00* | (2006.01) |

(52) U.S. Cl.
CPC ...... *C07K 16/2896* (2013.01); *A61K 39/3955* (2013.01); *A61P 35/00* (2018.01); *C07K 16/2818* (2013.01); *C12N 5/10* (2013.01); *A61K 2039/505* (2013.01); *C07K 2317/33* (2013.01); *C07K 2317/76* (2013.01); *C07K 2317/92* (2013.01)

(58) Field of Classification Search
CPC ............ C07K 16/2896; C07K 16/2818; C07K 2317/76; C07K 2317/33; C07K 2317/92; A61P 35/00; A61K 39/3955; A61K 2039/505; C12N 5/10
See application file for complete search history.

(56) References Cited

U.S. PATENT DOCUMENTS 8,557,777 B2   10/2013   Perambakam et al.

FOREIGN PATENT DOCUMENTS

| CN | 103242448 A | 8/2013 |
| CN | 104250302 A | 12/2014 |
| CN | 105175544 A | 12/2015 |
| WO | 2008/156712 A1 | 12/2008 |
| WO | 2010/031720 A2 | 3/2010 |
| WO | 2014/206107 A1 | 12/2014 |
| WO | 2016/014553 A1 | 1/2016 |

OTHER PUBLICATIONS

Almagro & Fransson, Frontiers in Bioscience 2008; 13:1619-33. (Year: 2008).*
De Genst et al., Developmental and Comparative Immunology, 2006, 30:187-98. (Year: 2006).*
Ward et al., Nature, 1989, 341:544-546. (Year: 1989).*
Barthelemy et al., Journal of Biological Chemistry, 2008, 283:3639-3654. (Year: 2008).*
Choi et al., 2011, Molecular BioSystems, 2011, 7:3327-334. (Year: 2011).*
Griffiths et al., The EMBO Journal, 1993, 12:725-734. (Year: 1993).*
Klimka et al., British Journal of Cancer, 2000, 83:252-260. (Year: 2000).*
Beiboer et al., Journal of Molecular Biology, 2000, 296:833-849. (Year: 2000).*
International Search Report (ISR) dated Apr. 25, 2017 for Application No. PCT/CN2017/072190.
Written Opinion dated Apr. 25, 2017 for Application No. PCT/CN2017/072190.
Espacenet English Abstract of CN 104250302 A.
Espacenet English Abstract of CN 103242448 A.
Espacenet English Abstract of CN 105175544 A.
Zhiyu Huang et al. "Clinical Research Progress of Anti PD-1/PD-L1 Monoclonal Antibody in the Treatment of Lung Cancer": Chinese Journal of Lung Cancer: vol. 11: No. 18: Nov. 30, 2015 (Nov. 30, 2015): ISSN: 1009-3419: pp. 706-713, see the whole document.
Naiyer A Rizvi, et al. "Activity and safety ofnivolumab, an anti-PD-1 immune check-point inhibitor, for patients with advanced, refractory squamous non-small-cell lung cancer (CheckMate 063): a phase 2, single-arm trial": LANCET ONCOLOGY: vol. 3: No. 16: Mar. 31, 2015 (Mar. 31, 2015): ISSN: 1470-2045: pp. 257-265, see the whole document.
European Search Report for counterpart 17746860.0•1111 / 3411410 PCT/CN2017072190.
Changyu Wang et al, : In Vitro Characterization of the Anti-PD-1 Antibody Nivolumab, BMS-936558, and In Vivo Toxicology in Non-Human Primates; Cancer Immunology Research, US, (May 28, 2014), vol. 2, No. 9, doi:10.1158/2326-6066.CIR-14-0040, ISSN 2326-6066, pp. 846-856, XP055563054 [AD] 1-14 * abstract * * p. OF8, paragraph 1st—p. OF9 * DOI: http://dx.doi.org/10.1158/2326-6066.CIR-14-0040.

(Continued)

*Primary Examiner* — Julie Wu
*Assistant Examiner* — Cheom-Gil Cheong
(74) *Attorney, Agent, or Firm* — Ladas & Parry LLP

(57) ABSTRACT

The present invention relates to antibodies that bind human programmed cell death 1 (PD-1), and may be useful for treating cancer alone and in combination with chemotherapy and other cancer therapeutics.

16 Claims, No Drawings

Specification includes a Sequence Listing.

(56) References Cited

OTHER PUBLICATIONS

Leila Khoja et al.; Pembrolizumab; Journal for Immunotherapy of Cancer; (Dec. 18, 2015), vol. 348, No. (Suppl 3), doi:10.1186/s40425-015-0078-9, p. 124, XP055316831 DOI: http://dx.doi.org/10.1186/s40425-015-0078-9.

James Larkin et al.; Combined Nivolumab and Ipilimumab or Monotherapy in Untreated Melanoma: The New England Journal of Medicine;—NEJM—, US, (Jul. 2, 2015), vol. 373, No. 1, doi:10.1056/NEJMoa1504030, ISSN 0028-4793, pp. 23-34, XP055553658 DOI: http://dx.doi.org/10.1056/NEJMoa1504030.

Dr Naiyer A Rizvi, et al.; Activity and safety of nivolumab, an anti-PD-1 immune checkpoint inhibitor, for patients with advanced, refractory squamous non-small-cell lung cancer (CheckMate 063); a phase 2, single-arm trial, Lancet Oncology, (Mar. 31, 2015), vol. 3, No. 16, doi:10.1016/S1470-2045(15)70054-9, pp. 257-265, XP055404123 DOI: http://dx.doi.org/10.1016/S1470-2045(15)70054-9.

Omid Hamid et al.; Anti-programmed death-1 and anti-programmed death-ligand 1 antibodies in cancer therapy; Expert Opinion on Biological The, Informa Healthcare, UK, (Jun. 1, 2013), vol. 13, No. 6, doi:10.1517/14712598.2013.770836, ISSN 1744-7682, pp. 847-861, XP008170016 DOI: http://dx.doi.org/.

Ikebuchi Ryoyo et al.; Molecular cloning and expression analysis of bovine programmed death-1, Microbiology and Immunology, JP, (Jan. 1, 2010), vol. 54, doi:10.1111/j.1348-0421.2010.00208.x, ISSN 0385-5600, pp. 291-298, XP055549033 [T] * abstract * DOI: http://dx.doi.org/10.1111/j.1348-0421.2010.00208.x.

Li Dong et al.; Epitope mapping reveals the binding mechanism of a functional antibody cross-reactive to both human and murine programmed death 1; MABS, (Mar. 16, 2017), vol. 9, No. 4, pp. 628-637, XP009514145 [IP] 1-14 * abstract * * p. 628-p. 637 * DOI: http://dx.doi.org/10.1080/19420862.2017.1296612.

Fu Jie et al.: Preclinical evaluation of the efficacy, pharmacokinetics and immunogenicity of JS-001, a programmed cell death protein-1 (PD-1) monoclonal antibody; ACTA Pharmacologica Sinica, (Mar. 13, 2017), vol. 38, No. 5, pp. 710-718, XP009514147 [AP] 1-14 * abstract * DOI: http://dx.doi.org/10.1038/aps.2016.161.

Omid Hamid, et al.; Safety and Tumor Reponses with Lambrolizumab (Anti-PD-1) in Melanoma; The New England and Journal of Medicine; Jul. 11, 2013; pp. 134-144.

Patricia Estep et al.; High throughput solution-based measurement of antibody-antigen affinity and epitope binning; mAbs 5:2, 270-278; Mar./Apr. 2013; © 2013 Landes Bioscience; vol. 5 Issue 2; pp. 270-278.

Murray P. Deutscher; Maintaining Protein Stability; Methods in Enzymology; vol. 182; (1990) pp. 83-89.

* cited by examiner

PD-1 ANTIBODIES

RELATED APPLICATION

This application is a national phase entry under 35 USC, 371 of International Patent Application No.: PCT/CN2017/072190 filed on 23 Jan. 2017, which claims priority from application No. PCT/CN2016/073169 filed on 2 Feb. 2016 the entire contents of which are incorporated herein by reference.

The present invention relates to the field of medicine. More particularly, the present invention relates to antibodies that bind human programmed cell death 1 (PD-1), and may be useful for treating cancer alone and in combination with chemotherapy and other cancer therapeutics.

Tumor cells escape detection and elimination by the immune system through multiple mechanisms. Immune checkpoint pathways are used in self-tolerance maintenance and activated T cell control, but cancer cells can use the pathways to prevent destruction. The PD-1/human programmed cell death 1 ligand 1 (PD-L) pathway is one such immune checkpoint. Human PD-1 is found on T cells, and the binding of PD-L1 and human programmed cell death 1 ligand 2 (PD-L2) to PD-1 inhibits T cell proliferation and cytokine production. Tumor cell production of PD-L1 and PD-L2 can therefore allow escape from T cell surveillance.

A fully human IgG4 (S228P) antibody against human PD-1, nivolumab, has been shown to inhibit the binding of PD-1 to PD-L and PD-L2, and has been tested in various clinical trials. (Wang et al., Cancer Immunol Res (2014) 2(9):846). A humanized IgG4 (S228P) antibody against PD-1, pembrolizumab (formerly lambrolizumab), has been shown to inhibit the binding of PD-1 to PD-L1 and PD-L2, and has been tested in various clinical trials. (WO2008156712 and Hamid et al., N Engl J Med (2013) 369:2).

There remains a need to provide alternative antibodies that bind and neutralize human PD-1 interaction with PD-L1 and PD-L2. In particular, there remains a need to provide antibodies that bind human PD-1 with high affinity but with different features than clinically approved PD-1 antibodies, such as binding to mouse and human PD-1. Further, there remains a need to provide antibodies that bind human PD-1 with affinity similar to clinically approved PD-1 but bind human PD-1 differently. Also, there remains a need to provide antibodies that more effectively block the human PD-1 interaction with PD-L1 and PD-L2 than certain prior art antibodies. Better blocking can translate into greater in vivo activity or lower required dosing amounts.

Certain antibodies of the present invention block the human PD-1 to PD-L1 and PD-L2 interactions in CHO cells more effectively than nivolumab and pembrolizumab. Furthermore, certain antibodies of the present invention bind murine PD-1 on CHO cells whereas nivolumab and pembrolizumab binding to murine PD-1 is not detected.

Accordingly, in some embodiments the present invention provides an antibody that binds human PD-1 (SEQ ID NO: 1), comprising a light chain (LC) and a heavy chain (HC), wherein the light chain comprises light chain complementarity determining regions LCDR1, LCDR2, and LCDR3 consisting of the amino acid sequences RASQSVSSYLA (SEQ ID NO: 14), YDASKRAT (SEQ ID NO: 15), and DQRNNWPLT (SEQ ID NO: 16), respectively, and wherein the heavy chain comprises heavy chain complementarity determining regions HCDR1, HCDR2, and HCDR3, wherein HCDR1 consists of the amino acid sequence:

a. KASGYTFTSYYMH, (SEQ ID NO: 2)

b. KASGYTFEGYYMH, (SEQ ID NO: 3)

c. KASGYTFTAQYMH, (SEQ ID NO: 4)

d. KASGYTFEKYYMH, (SEQ ID NO: 5)

e. KASGYTFTSNYMH, (SEQ ID NO: 6)
or f. KASGYTFSAYYMH (SEQ ID NO: 7)

wherein HCDR2 consists of the amino acid sequence:

a. IINPSGGSTSYAQKFQG, (SEQ ID NO: 8)

b. IINPEGGETSYAQKFQG, (SEQ ID NO: 9)

c. IINPSGGETGYAQKFQG, (SEQ ID NO: 10)

d. IINPSEGSTGYAQKFQG, (SEQ ID NO: 11)
or e. IINPDGGSTGYAQKFQG; (SEQ ID NO: 12)

and wherein HCDR3 consists of the amino acid sequence AKEGVADGYGLVDV (SEQ ID NO: 13).

In some embodiments, the present invention provides an antibody that binds human PD-1 (SEQ ID NO: 1), wherein LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and wherein HCDR1, HCDR2, and HCDR3 consist of the amino acid sequences KASGYTFTSYYMH (SEQ ID NO: 2), IINPSGGSTSYAQKFQG (SEQ ID NO: 8), and AKEGVADGYGLVDV (SEQ ID NO: 13), respectively.

In some embodiments, the present invention provides an antibody that binds human PD-1 (SEQ ID NO: 1), wherein LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and wherein HCDR1, HCDR2, and HCDR3 consist of the amino acid sequences KASGYTFEGYYMH (SEQ ID NO: 3), IINPEGGETSYAQKFQG (SEQ ID NO: 9), and AKEGVADGYGLVDV (SEQ ID NO: 13), respectively.

In some embodiments, the present invention provides an antibody that binds human PD-1 (SEQ ID NO: 1), wherein LCDR1, LCDR2, and LCDR3 consist of the amino acid sequences RASQSVSSYLA (SEQ ID NO: 14), YDASK- RAT (SEQ ID NO: 15), and DQRNNWPLT (SEQ ID NO: 16), respectively, and wherein HCDR1, HCDR2, and HCDR3 consist of the amino acid sequences KASGYTFTAQYMH (SEQ ID NO: 41) IINPSGGETGYAQKFQG (SEQ ID NO: 10), and AKEGVADGYGLVDV (SEQ ID NO: 13), respectively.

In some embodiments, the present invention provides an antibody that binds human PD-1 (SEQ ID NO: 1), wherein LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and wherein HCDR1, HCDR2, and HCDR3 consist of the amino acid sequences KASGYTFEKYYMH (SEQ ID NO: 5), IINPDGGSTGYAQKFQG (SEQ ID NO: 12), and AKEGVADGYGLVDV (SEQ ID NO: 13), respectively.

In some embodiments, the present invention provides an antibody that binds human PD-1 (SEQ ID NO: 1), wherein LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and wherein HCDR1, HCDR2, and HCDR3 consist of the amino acid sequences KASGYTFTSNYMH (SEQ ID NO: 6), IINPSEGSTGYAQKFQG (SEQ ID NO: 11), and AKEGVADGYGLVDV (SEQ ID NO: 13), respectively.

In some embodiments, the present invention provides an antibody that binds human PD-1 (SEQ ID NO: 1), wherein LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and wherein HCDR1, HCDR2, and HCDR3 consist of the amino acid sequences KASGYTFSAYYMH (SEQ ID NO: 7), IINPDGGSTGYAQKFQG (SEQ ID NO: 12), and AKEGVADGYGLVDV (SEQ ID NO: 13), respectively.

In some embodiments, the present invention provides an antibody, comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 23, and the HCVR has the amino acid sequence given in SEQ ID NO: 17, SEQ ID NO: 18, SEQ ID NO: 19, SEQ ID NO: 20, SEQ ID NO: 21, or SEQ ID NO: 22.

In a further embodiment, the present invention provides an antibody, wherein the LCVR has the amino acid sequence given in SEQ ID NO: 23, and the HCVR has the amino acid sequence given in SEQ ID NO: 17.

In a further embodiment, the present invention provides an antibody, wherein the LCVR has the amino acid sequence given in SEQ ID NO: 23, and the HCVR has the amino acid sequence given in SEQ ID NO: 18.

In a further embodiment, the present invention provides an antibody, wherein the LCVR has the amino acid sequence given in SEQ ID NO: 23, and the HCVR has the amino acid sequence given in SEQ ID NO: 19.

In a further embodiment, the present invention provides an antibody, wherein the LCVR has the amino acid sequence given in SEQ ID NO: 23, and the HCVR has the amino acid sequence given in SEQ ID NO: 20.

In a further embodiment, the present invention provides an antibody, wherein the LCVR has the amino acid sequence given in SEQ ID NO: 23, and the HCVR has the amino acid sequence given in SEQ ID NO: 21.

In a further embodiment, the present invention provides an antibody, wherein the LCVR has the amino acid sequence given in SEQ ID NO: 23, and the HCVR has the amino acid sequence given in SEQ ID NO: 22.

In some embodiments, the present invention provides an antibody, wherein the LC has the amino acid sequence given in SEQ ID NO: 30, and the HC has the amino acid sequence given in SEQ ID NO: 24, SEQ ID NO: 25, SEQ ID NO: 26, SEQ ID NO: 27, SEQ ID NO: 28, or SEQ ID NO: 29.

In a further embodiment, the present invention provides an antibody, wherein the LC has the amino acid sequence given in SEQ ID NO: 30, and the HC has the amino acid sequence given in SEQ ID NO: 24.

In a further embodiment, the present invention provides an antibody, wherein the LC has the amino acid sequence given in SEQ ID NO: 30, and the HC has the amino acid sequence given in SEQ ID NO: 25.

In a further embodiment, the present invention provides an antibody, wherein the LC has the amino acid sequence given in SEQ ID NO: 30, and the HC has the amino acid sequence given in SEQ ID NO: 26.

In a further embodiment, the present invention provides an antibody, wherein the LC has the amino acid sequence given in SEQ ID NO: 30, and the HC has the amino acid sequence given in SEQ ID NO: 27.

In a further embodiment, the present invention provides an antibody, wherein the LC has the amino acid sequence given in SEQ ID NO: 30, and the HC has the amino acid sequence given in SEQ ID NO: 28.

In a further embodiment, the present invention provides an antibody, wherein the LC has the amino acid sequence given in SEQ ID NO: 30, and the HC has the amino acid sequence given in SEQ ID NO: 29.

In some embodiments, the present invention provides an antibody, comprising two light chains and two heavy chains, wherein each light chain has the amino acid sequence given in SEQ ID NO: 30, and each heavy chain has the amino acid sequence given in SEQ ID NO: 24, SEQ ID NO: 25, SEQ ID NO: 26, SEQ ID NO: 27, SEQ ID NO: 28, or SEQ ID NO: 29.

In a further embodiment, the present invention provides an antibody, wherein each light chain has the amino acid sequence given in SEQ ID NO: 30, and each heavy chain has the amino acid sequence given in SEQ ID NO: 24.

In a further embodiment, the present invention provides an antibody, wherein each light chain has the amino acid sequence given in SEQ ID NO: 30, and each heavy chain has the amino acid sequence given in SEQ ID NO: 25.

In a further embodiment, the present invention provides an antibody, wherein each light chain has the amino acid sequence given in SEQ ID NO: 30, and each heavy chain has the amino acid sequence given in SEQ ID NO: 26.

In a further embodiment, the present invention provides an antibody, wherein each light chain has the amino acid sequence given in SEQ ID NO: 30, and each heavy chain has the amino acid sequence given in SEQ ID NO: 27.

In a further embodiment, the present invention provides an antibody, wherein each light chain has the amino acid sequence given in SEQ ID NO: 30, and each heavy chain has the amino acid sequence given in SEQ ID NO: 28.

In a further embodiment, the present invention provides an antibody, wherein each light chain has the amino acid sequence given in SEQ ID NO: 30, and each heavy chain has the amino acid sequence given in SEQ ID NO: 29.

In an embodiment, the present invention provides an antibody, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

In an embodiment, the present invention provides an antibody, wherein the antibody is glycosylated.

In some embodiments, the present invention provides an antibody that binds both human PD-1 and mouse PD-1. In a further embodiment, the present invention provides an antibody that is an antagonistic antibody and that binds both human PD-1 and mouse PD-1. In a further embodiment, the present invention provides an antibody that binds both human PD-1 and mouse PD-1 with a Kd for each less than 400 pM. In a further embodiment, the present invention provides an antibody that binds both human PD-1 and mouse PD-1 with a Kd for each less than 200 pM.

In an embodiment, the present invention provides a pharmaceutical composition, comprising an antibody of the present invention, and an acceptable carrier, diluent, or excipient.

In an embodiment, the present invention provides a method of treating cancer, comprising administering to a patient in need thereof, an effective amount of an antibody of the present invention. In a further embodiment, the present invention provides a method of treating cancer, comprising administering to a patient in need thereof, an effective amount of an antibody of the present invention, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

In a further embodiment, these methods comprise the administration of an effective amount of the antibody of the present invention in simultaneous, separate, or sequential combination with one or more anti-tumor agents. Non-limiting examples of anti-tumor agents include ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab.

In a further embodiment, these methods comprise the administration of an effective amount of the compound of the present invention in simultaneous, separate, or sequential combination with one or more immuno-oncology agents. Non-limiting examples of immuno-oncology agents include nivolumab, ipilimumab, pidilizumab, pembrolizumab, tremelimumab, urelumab, lirilumab, atezolizumab, and durvalumab.

In an embodiment, the present invention provides an antibody of the present invention, for use in therapy. In an embodiment, the present invention provides an antibody of the present invention, for use in the treatment of cancer. In a further embodiment, the present invention provides an antibody of the present invention, for use in the treatment of cancer, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma. In a further embodiment, the present invention provides the antibody of the present invention for use in simultaneous, separate, or sequential combination with one or more anti-tumor agents. In a further embodiment, the present invention provides the antibody of the present invention for use in simultaneous, separate, or sequential combination with one or more anti-tumor agents selected from the group consisting of ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab, in the treatment of cancer.

In a further embodiment, the present invention provides the antibody of the present invention for use in simultaneous, separate, or sequential combination with one or more immuno-oncology agents. In a further embodiment, the present invention provides the antibody of the present invention for use in simultaneous, separate, or sequential combination with one or more immuno-oncology agents selected from the group consisting of nivolumab, ipilimumab, pidilizumab, pembrolizumab, tremelimumab, urelumab, lirilumab, atezolizumab, and durvalumab, in the treatment of cancer.

In a further embodiment, the present invention provides the use of an antibody of the present invention for the manufacture of a medicament for the treatment of cancer. In a further embodiment, the present invention provides the use of an antibody of the present invention for the manufacture of a medicament for the treatment of cancer, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

In a further embodiment, the present invention provides the use of an antibody of the present invention in the manufacture of a medicament for the treatment of cancer wherein said medicament is to be administered simultaneously, separately, or sequentially with one or more anti-tumor agents. In a further embodiment, the present invention provides the use of an antibody of the present invention in the manufacture of a medicament for the treatment of cancer wherein said medicament is to be administered simultaneously, separately, or sequentially with one or more anti-tumor agents selected from the group consisting of ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab.

An antibody of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in an antibody of the present invention.

An antibody of the present invention is designed to have engineered CDRs and have some portions of the antibody (all or parts of the frameworks, hinge regions, and constant regions) to be of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and those with engineered mutations. An antibody of the present invention may comprise framework, hinge, or constant regions derived from a fully human framework, hinge, or constant region containing one or more amino acid substitutions, deletions, or additions therein. Further, an antibody of the present invention is preferably substantially non-immunogenic in humans.

The antibody of the present invention is an IgG type antibody and has "heavy" chains and "light" chains that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, the antibody of the present invention contains an Fc portion which is derived from human $IgG_4$ Fc region because of a reduced ability to engage Fc receptor-mediated inflammatory mechanisms or to activate complement resulting in reduced effector function.

Certain antibodies of the present invention contain an $IgG_4$-Fc portion that has a serine to proline mutation at position 228. The S228P mutation is a hinge mutation that prevents half-antibody formation (phenomenon of dynamic exchange of half-molecules in $IgG_4$ antibodies).

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. There are currently three systems of CDR assignments for antibodies that are used for sequence delineation. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North et al., "A New Clustering of Antibody CDR Loop Conformations", Journal of Molecular Biology, 406, 228-256 (2011)) is based on affinity propagation clustering with a large number of crystal structures.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibody of the present invention may readily be produced in mammalian cells such as CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice*, 3rd Edition, Springer, NY (1994).

In another embodiment of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80%0 (on a molar basis) of the macromolecular species present, preferably more than 90%, and more preferably more than 95%.

The antibody of the present invention, or pharmaceutical compositions comprising the same, may be administered by parenteral routes (e.g., subcutaneous and intravenous). An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy*, $19^{th}$ ed. (1995), A. Gennaro et al., Mack Publishing Co.) and comprise an antibody, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease.

"Binds" as used herein in reference to the affinity of an antibody for human PD-1 is intended to mean, unless indicated otherwise, a $K_D$ of less than about $1 \times 10-6$ M, preferably, less than about $1 \times 10-9$ M as determined by common methods known in the art, including by use of MSD essentially as described herein.

For the purposes of the present disclosure, the term "high affinity" refers to a $K_D$ of less than about 150 pM for human PD-1 as determined by MSD. The $K_D$ values are established by binding kinetics as described in "Binding kinetics and affinity" in the Assays section.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

This invention is further illustrated by the following non-limiting example.

EXAMPLE 1: ANTIBODY EXPRESSION AND PURIFICATION

The polypeptides of the variable regions of the heavy chain and light chain, the complete heavy chain and light chain amino acid sequences of Antibody A-Antibody F, and the nucleotide sequences encoding the same, are listed below in the section entitled "Amino Acid and Nucleotide Sequences." In addition, the SEQ ID NOs for the light chain, heavy chain, light chain variable region, and heavy chain variable region of Antibody A-Antibody F are shown in Table 1.

The antibodies of the present invention, including, but not limited to, Antibody A-Antibody F can be made and purified essentially as follows. An appropriate host cell, such as HEK 293 or CHO, can be either transiently or stably transfected with an expression system for secreting antibodies using an optimal predetermined HC:LC vector ratio or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is greater than 95%. The product may be immediately frozen at −70° C. or may be lyophilized.

TABLE 1

| | SEQ ID NOs | | | | | |
|---|---|---|---|---|---|---|
| | Antibody A | Antibody B | Antibody C | Antibody D | Antibody E | Antibody F |
| HCVR | 17 | 18 | 19 | 20 | 21 | 22 |
| LCVR | 23 | 23 | 23 | 23 | 73 | 23 |

TABLE 1-continued

| | SEQ ID NOs | | | | | |
|---|---|---|---|---|---|---|
| | Antibody A | Antibody B | Antibody C | Antibody D | Antibody E | Antibody F |
| Heavy chain | 24 | 25 | 26 | 27 | 28 | 29 |
| Light chain | 30 | 30 | 30 | 30 | 30 | 30 |

Assays

Binding Kinetics and Affinity

The kinetics and equilibrium dissociation constant ($K_D$) for human PD-1 is determined for antibodies of the present invention using MSD, and bio-layer interferometry (ForteBio) assay methods.

As used herein, nivolumab is a human IgG4 PD-1 antibody transiently expressed in 293 HEK cells that utilizes the heavy chain and light chain sequences from Proposed INN: List 107 (CAS #946414-94-4). As used herein, pembrolizumab is a human IgG4 PD-1 antibody transiently expressed in 293 HEK cells that utilizes the heavy chain and light chain sequences from Proposed INN: List 72.

MSD Assay

Equilibrium affinity measurements are performed as previously described (Estep, P., et al., MAbs, 2013. 5(2): p. 270-8). Solution equilibrium titrations (SET) are performed in PBS+0.1% IgG-Free BSA (PBSF) where antigen (b-PD-1 monomer) is held constant at 10-100 pM and is incubated with 3- to 5-fold serial dilutions of Fab or mAbs starting at 5-100 nM (experimental condition is sample dependent). Antibodies diluted at 20 nM in PBS are coated onto standard bind MSD-ECL plates overnight at 4° C. or at room temperature for 30 min. Plates are blocked with BSA for 30 min whilst shaking at 700 rpm. Plates are then washed 3× with wash buffer (PBSF+0.05% Tween 20). SET samples are applied and incubated on the plates for 150 s with shaking at 700 rpm followed by one wash. Antigen captured on a plate is detected with 250 ng/mL sulfotag-labeled streptavidin in PBSF by incubation on the plate for 3 min. The plates are washed three times with wash buffer and are then read on the MSD Sector Imager 2400 instrument using 1× Read Buffer T with surfactant. The percent free antigen is plotted as a function of titrated antibody in Prism and fit to a quadratic equation to extract the KD. To improve throughput, liquid handling robots are used throughout MSD-SET experiments, including for SET sample preparation.

In experiments performed essentially as described in this assay, Antibody C and Antibody E, in an IgG1 format and expressed in yeast, bind human PD-1 with a $K_D$ of 120 pM and 91 pM, respectively. Pembrolizumab and nivolumab bind PD-1 with a $K_D$ of 130 pM and 640 pM respectively. Avidity measurements for Antibody C and Antibody E result in a $K_D$ of approximately 9 pM and 22 pM, respectively, to human PD-1. Pembrolizumab and nivolumab bind human PD-1 with a $K_D$ of approximately 3 pM and 5 pM respectively. Antibody C and Antibody E, in an IgG1 format and expressed in yeast, bind murine PD-1 with a $K_D$ of 1900 pM and 1100 pM, respectively. Avidity measurements for Antibody C and Antibody E result in a $K_D$ of approximately 130 pM and 330 pM, respectively, to murine PD-1.

TABLE 1A

Binding by MSD of antibodies of the invention in IgG1 format

| Name | Monovalent KD (M) against human PD-1 | Avid KD (M) against human PD-1 | Monovalent KD (M) against murine PD-1 | Avid KD (M) against murine PD-1 |
|---|---|---|---|---|
| Antibody A | 4.90E−09 | 4.90E−11 | 9.60E−09 | P.F. |
| Antibody B | 1.30E−10 | 1.40E−11 | 2.70E−09 | 3.80E−10 |
| Antibody C | 1.20E−10 | 9.30E−12 | 1.90E−09 | 1.30E−10 |
| Antibody D | 3.00E−10 | 3.50E−11 | 2.30E−09 | P.F. |
| Antibody E | 9.10E−11 | 2.20E−11 | 1.10E−09 | 3.30E−10 |
| Antibody F | 1.70E−10 | 1.80E−11 | 1.20E−09 | 4.40E−10 |
| Pembrolizumab | 1.30E−10 | 3.00E−12 | N.D. | N.D. |
| Nivolumab | 6.40E−10 | 5.10E−12 | N.D. | N.D. |

(P.F.: poor fit; N.D.: none detected)

Bio-Layer Interferometry

ForteBio affinity measurements were performed generally as previously described (Estep, P., et al., *High throughput solution-based measurement of antibody-antigen affinity and epitope binning*. MAbs, 2013. 5(2): p. 270-8.). Briefly, ForteBio affinity measurements were performed by loading IgGs online onto AHQ sensors. Sensors were equilibrated off-line in assay buffer for 30 min and then monitored on-line for 60 seconds for baseline establishment. Sensors with loaded IgGs were exposed to 100 nM antigen for 5 min, afterwards they were transferred to assay buffer for 5 min for off-rate measurement. Kinetics was analyzed using the 1:1 binding model.

TABLE 2

Binding by Bio-light interferometry of antibodies of the invention in IgG1 format

| | Monovalent $K_D$ (M) Fab in solution, human PD-1_Fc on sensor tip | Monovalent $K_D$ (M) human PD-1_HIS in solution, IgG on sensor tip | Monovalent $K_D$ (M) Fab in solution, cyno PD-1_Fc on sensor tip | Monovalent $K_D$ (M) Fab in solution, murine PD-1_Fc on sensor tip |
|---|---|---|---|---|
| Antibody A | 1.60E−08 | 4.30E−09 | 1.40E−08 | 3.30E−08 |
| Antibody B | 2.70E−09 | 1.40E−09 | 3.70E−09 | 1.70E−08 |
| Antibody C | 2.00E−09 | 1.00E−09 | 2.40E−09 | 1.00E−08 |
| Antibody D | 3.40E−09 | 1.90E−09 | 4.40E−09 | 7.80E−09 |
| Antibody E | 2.70E−09 | 1.20E−09 | 3.30E−09 | 7.60E−09 |
| Antibody F | 3.00E−09 | 1.60E−09 | 3.60E−09 | 6.10E−09 |
| Pembrolizumab | 2.00E−09 | 2.00E−09 | 4.70E−10 | N.D. |
| Nivolumab | 1.70E−09 | 4.10E−09 | 1.20E−09 | N.D. |

(N.D.: none detected)

In experiments performed essentially as described in this assay, Antibody C and Antibody E, in an IgG1 format and expressed in yeast, bind human PD-1_Fc with a $K_D$ similar to nivolumab and pembrolizumab when PD-1_Fc was on the sensor tip. When the antibody was on the sensor tip, Antibody C and Antibody E, in an IgG1 format and expressed in yeast, bind human PD-1_Fc with a $K_D$ similarly to nivolumab and pembrolizumab. Antibody C and Antibody E, in an IgG1 format and expressed in yeast, bind cyno PD-1_Fc with a similar $K_D$ to nivolumab and pembrolizumab. Antibody C and Antibody E, in an IgG1 format and expressed in yeast, bind murine PD-1_Fc whereas no binding was detected with nivolumab and pembrolizumab.

Binding to Human and Murine PD-1 on CHO Cells

The binding of an antibody of the present invention to human PD-1 may be measured in a flow cytometry assay.

CHO cells ($0.2 \times 10^6$) are incubated with the experimental antibody from 100 nM titrated 14× by a factor of 2 to the lowest concentration of 6.1 pM for 30 min in PBS 1% BSA on ice. Cells are then washed 3×, and are incubated with a secondary antibody (PE-labelled, at final concentration of 5 μg/ml) in PBS 1% BSA for 30 min on ice (protected from light). Cells are washed 3× and analyzed via flow cytometry. Flow cytometry is performed on an Accuri C6 system (BD Biosciences) and MFIs are calculated on the C6 software. EC50 s are calculated on Graphpad software.

In experiments performed essentially as described in this assay, Antibody A, Antibody C, and Antibody E, in an IgG1 format and expressed in yeast bind human PD-1 in a dose-dependent manner, with an EC50 value (n=1) of 10.22 nM, 4.115 nM and 4.587 nM, respectively, and pembrolizumab binds human PD-1 with an EC50 value (n=1) of 0.6921 nM and nivolumab with an EC50 value (n=1) of 0.8057 nM.

Antibody A, B, C, D, E, and F, in an IgG1 format and expressed in yeast bind to murine PD-1 in a dose dependent manner with an EC50 of 11.01 nM, 6.135 nM, 2.884 nM, 9.259 nM, and 5.044 nM, and 5.855 nM, respectively, whereas no binding was detected for nivolumab or pembrolizumab.

Blocking of Human PD-1 to PD-L1 and PD-L2 in CHO Cells.

The ability of an antibody of the present invention to block binding of human PD-1 to PD-L1 and PD-L2 may be measured by flow cytometry.

CHO cells $0.2 \times 10^6$ are incubated with the experimental antibody (100 nM) for 30 min in PBS 1% BSA on ice. Cells are then washed 3×, and are incubated with PD-L2 linked with NHS-Fluorescein (Promega) in PBS 1% BSA for 30 min on ice (protected from light). Cells are washed 3× and analyzed via flow cytometry. Flow cytometry is performed on an Accuri C6 system (BD Biosciences) and MFIs are calculated on the C6 software. EC50 s are calculated on Graphpad software.

In experiments performed essentially as described in this assay, Antibody C and Antibody E (IgG1 format expressed in yeast) blocked human PD-L2-FITC binding, resulting in an MFI of 30,123.4 and 38,682.1, respectively, as compared to control IgG which resulted in an MFI of 182,959.1. Pembrolizumab and nivolumab resulted in MFI's of 46,245.9 and 54,509.8 respectively.

TABLE 3

Blocking of human PD-1 on CHO cells

| Test Sample | MFI (PD-L2-FITC) |
|---|---|
| Cells only | 33,449.7 |
| No IgG | 199,716.0 |
| IgG Control | 182,959.1 |
| Nivolumab | 54,509.8 |
| Pembrolizumab | 46,245.9 |
| Antibody A | 90,866.5 |
| Antibody C | 30,123.4 |
| Antibody E | 38,682.1 |

Mixed Lymphocyte Reaction

The blocking of PD-1 signals by antibodies of the present invention may be evaluated by measuring the release of inhibitory signals during T cell activation.

$2 \times 10^6$ PBMC are plated per well in a 6 well tissue culture plate or T25 tissue culture flask in complete T cell media. Cells are incubated for 2-3 hours, to allow for adherence of monocytes. If adherence is insufficient, serum free media is used. Unattached cells are removed by gently swirling the flask with fresh media 3×.

Immature myeloid DCs are generated by culturing monocytes ($1 \times 10^6$ cells/ml) from PBMC in X-VIVO 15 media containing 1% AB serum, 10 mM HEPES, 50 pM β-Me, IL-4 (1000 U/ml) and GM-CSF (1000 U/ml), or 25-50 ng/ml of each. After 2 days fresh medium supplemented with IL-4 and GM-CSF is added. On Day 5, cells are either frozen or maturation is induced by adding a stimulation cocktail containing rTNFa (1000 U/ml), IL-1b (5 ng/ml), IL-6 (10 ng/ml) and 1 pM $PGE_2$ for 2 days at a cell density of $3 \times 10^5$ cells/ml.

T cell Isolation is performed as per manufacturer's instructions in the Untouched CD4+ T cell isolation kit (Invitrogen). A magnet fitted with a 1.5 ml tube rack is used to remove unwanted magnetic beads (QIAGEN). 100,000-200,000 isolated T cells are mixed with 10,000-20,000 allogeneic moDCs in a total volume of 200 μl in 96-round bottom tissue culture plates for 4-5 days at 37° C. T cells are stimulated using anti-CD3/CD28 DynaBeads at a ratio of 3:1 (cells:beads) as a positive control; beads are prepared as per the manufacturer's instructions. Test antibodies are added at the beginning of the MLR and incubated throughout the culture period. Detection of IL-2 and IFN-γ is carried out as per manufacturer's instructions (eBioscience). OD measurements are determined on a Multiskan FC system (Thermo).

In experiments performed essentially as described in this assay, Antibody C and Antibody E increase IL-2 and IFNg secretion by activated T cells in the mixed lymphocyte reaction with equivalent potency as compared with nivolumab and pembrolizumab.

TABLEd

IL-2 secretion fold change vs. IgG control

| IgG | Concentrations of IgG | | | | |
|---|---|---|---|---|---|
| | 100 nM | 10 nM | 1 nM | 0.1 nM | 0.01 nM |
| Pembrolizumab | 2.03 | 2.49 | 2.04 | 1.47 | 1.06 |
| Nivolumab | 2.37 | 2.44 | 1.72 | 1.26 | 1.09 |
| Antibody A | 2.28 | 1.87 | 1.23 | 1.15 | 1.37 |
| Antibody C | 2.62 | 2.29 | 1.83 | 1.15 | 1.01 |
| Antibody E | 3.20 | 2.61 | 1.95 | 1.21 | 1.13 |

| | Cytokine in supernatant | Concentrations of IgG | | | | |
|---|---|---|---|---|---|---|
| | | 100 nM | 10 nM | 1 nM | 0.1 nM | 0.01 nM |
| IgG control | IL-2 (pg/ml) | 619.16 | 521.57 | 500.33 | 508.82 | 515.02 |
| | Stdev. (pg/ml) | 18.53 | 4.13 | 25.45 | 18.92 | 18.33 |
| Pembrolizumab | IL-2 (pg/ml) | 1257.59 | 1299.83 | 1021.63 | 749.33 | 545.48 |
| | Stdev. (pg/ml) | 27.37 | 13.42 | 37.56 | 33.53 | 11.21 |
| Nivolumab | IL-2 (pg/ml) | 1469.85 | 1274.69 | 858.20 | 641.13 | 562.30 |
| | Stdev. (pg/ml) | 55.01 | 68.79 | 44.24 | 23.40 | 33.04 |
| Antibody A | IL-2 (pg/ml) | 1410.46 | 975.38 | 617.86 | 585.50 | 707.77 |
| | Stdev. (pg/ml) | 41.38 | 27.88 | 49.01 | 8.39 | 27.93 |
| Antibody C | IL-2 (pg/ml) | 1622.02 | 1194.17 | 913.62 | 587.10 | 518.69 |
| | Stdev. (pg/ml) | 49.88 | 46.17 | 30.18 | 42.17 | 12.79 |
| Antibody E | IL-2 (pg/ml) | 1983.95 | 1361.71 | 977.51 | 614.19 | 580.24 |
| | Stdev. (pg/ml) | 119.32 | 57.80 | 20.95 | 15.81 | 12.83 |

TABLE 5

IFNg secretion fold change vs. IgG control

| IgG | Concentrations of IgG | | | | |
|---|---|---|---|---|---|
| | 100 nM | 10 nM | 1 nM | 0.1 nM | 0.01 nM |
| Pembrolizumab | 1.78 | 1.77 | 1.76 | 1.99 | 1.03 |
| Nivolumab | 1.97 | 1.88 | 1.58 | 1.53 | 0.84 |
| Antibody A | 1.52 | 1.37 | 1.11 | 1.49 | 1.49 |
| Antibody C | 1.84 | 1.79 | 1.82 | 1.50 | 0.97 |
| Antibody E | 1.76 | 2.01 | 1.86 | 1.26 | 0.96 |

TABLE 5-continued

| | | IFNg secretion fold change vs. IgG control | | | | |
|---|---|---|---|---|---|---|
| | Cytokine in | Concentrations of IgG | | | | |
| | supernatant | 100 nM | 10 nM | 1 nM | 0.1 nM | 0.01 nM |
| IgG control | IFNγ (pg/ml) | 14936.03 | 13497.03 | 11603.92 | 11007.43 | 14881.91 |
| | Stdev. (pg/ml) | 331.65 | 912.08 | 815.69 | 1400.66 | 453.67 |
| Pembrolizumab | IFNγ (pg/ml) | 26598.52 | 23903.29 | 20390.76 | 21894.58 | 15326.75 |
| | Stdev. (pg/ml) | 1143.84 | 409.35 | 1274.53 | 1038.25 | 280.19 |
| Nivolumab | IFNγ (pg/ml) | 29482.91 | 25333.89 | 18296.62 | 16820.33 | 12487.21 |
| | Stdev. (pg/ml) | 3935.40 | 3201.10 | 203.28 | 725.93 | 613.05 |
| Antibody A | IFNγ (pg/ml) | 22631.06 | 18442.75 | 12915.14 | 16368.19 | 22121.86 |
| | Stdev. (pg/ml) | 712.64 | 3029.49 | 1683.58 | 580.07 | 160.46 |
| Antibody C | IFNγ (pg/ml) | 27443.11 | 24094.79 | 21136.75 | 16460.20 | 14382.09 |
| | Stdev. (pg/ml) | 1036.81 | 888.47 | 936.17 | 914.50 | 929.68 |
| Antibody E | IFNγ (pg/ml) | 26262.69 | 27124.92 | 21575.50 | 13825.35 | 14331.43 |
| | Stdev. (pg/ml) | 898.53 | 1884.76 | 508.65 | 513.84 | 1708.45 |

Tumor Model

The antibodies of the present invention can be measured for in vivo immunomodulatory activity with the MC38 in vivo tumor mode. C57B1/6 mice are inoculated subcutaneously with MC38 murine colon cancer cells $2 \times 10^6$ per mouse to establish the tumor-bearing model. Mice are selected 10 days after tumor inoculation with tumor volumes between 34.81 mm$^3$~148.24 mm$^3$ and then divided into five groups. These groups include a control group, RMP1-14 (Bio X Cell), Compound C-2.5, Compound C-5, and Compound C-10 (n=10). RMP1-14 group is given a dose of 10 mg/kg. Compound C-2.5, Compound C-5, and Compound C-10 groups are given 2.5 mg/kg, 5 mg/kg and 10 mg/kg of 11430 respectively (Compound C S228P IgG4 produced in HEK293 cells).

The control group receives an equal volume of saline, and all groups are dosed via intraperitoneal injection, dose frequency of 2 times weekly for 4 weeks. Weekly monitoring of animal body weight, and tumor volume (using formula $V=L \times W^2/2$) is conducted. After the experiment, tumors are photographed and weighed to calculate tumor weight and to calculate relative tumor inhibition.

In experiments performed essentially as described in this assay, the results show that administration of RMP1-14 and Compound C has no effect on animal weight. RMP1-14 and Compound C show significant anti-tumor effect after one week of administration. The three Compound C dose groups have higher anti-tumor (tumor volume reducing) effects compared to the RMP1-14 group. In groups Compound C-2.5 and Compound C-10, 1 and 2 mice, respectively, had complete tumor regression. After treatment, tumor weight is significantly reduced by the RMP1-14 and three Compound C groups as compared to the control group. RMP1-14 group had a relative tumor inhibition value of 55.03%, with Compound C-2.5, Compound C-5, and Compound C-10 groups with relative tumor inhibition values of 69.70%, 76.53%, and 81.04%, respectively, showing a dose-dependent manner of Compound C on tumor weight. Thus, Compound C has significant anti-tumor efficacy in tumor-bearing mice, and has better effect than the positive control clone RMP1-14.

```
                Amino Acid and Nucleotide Sequences
SEQ ID NO: 1 (human PD-1)
MQIPQAPWPVVWAVLQLGWRPGWFLDSPDRPWNPPTFSPALLVVTEGDNATFT
CSFSNTSESFVLNWYRMSPSNQTDKLAAFPEDRSQPGQDCRFRVTQLPNGRDFH
MSVVRARRNDSGTYLCGAISLAPKAQIKESLRAELRVTERRAEVPTAHPSPSPRPA
GQFQTLVVGVVGGLLGSLVLLVWVLAVICSRAARGTIGARRTGQPLKEDPSAVP
VFSVDYGELDFQWREKTPEPPVPCVPEQTEYATIVFPSGMSTSSPARRGSADGPR
SAQPLRPEDGHCSWPL SEQ ID NO: 2 (HCDR1 of Antibody A)
KASGYTFTSYYMH SEQ ID NO: 3 (HCDR1 of Antibody B)
KASGYTFEGYYMH SEQ ID NO: 4 (HCDR1 of Antibody C)
KASGYTFTAQYMH
```

Amino Acid and Nucleotide Sequences

SEQ ID NO: 5 (HCDR1 of Antibody D)
KASGYTFEKYYMH

SEQ ID NO: 6 (HCDR1 of Antibody E)
KASGYTFTSNYMH

SEQ ID NO: 7 (HCDR1 of Antibody F)
KASGYTFSAYYMH

SEQ ID NO: 8 (HCDR2 of Antibody A)
IINPSGGSTSYAQKFQG

SEQ ID NO: 9 (HCDR2 of Antibody B)
IINPEGGETSYAQKFQG

SEQ ID NO: 10 (HCDR2 of Antibody C)
IINPSGGETGYAQKFQG

SEQ ID NO: 11 (HCDR2 of Antibody E)
IINPSEGSTGYAQKFQG

SEQ ID NO: 12 (HCDR2 of Antibody D and F)
IINPDGGSTGYAQKFQG

SEQ ID NO: 13 (HCDR3 of Antibody A-F)
AKEGVADGYGLVDV

SEQ ID NO: 14 (LCDR1 of Antibody A-F)
RASQSVSSYLA

SEQ ID NO: 15 (LCDR2 of Antibody A-F)
YDASKRAT

SEQ ID NO: 16 (LCDR3 of Antibody A-F)
DQRNNWPLT

SEQ ID NO: 17 (HCVR of Antibody A)
QVQLVQSGAEVKKPGASVKVSCKASGYTFTSYYMHWVRQAPGQGLEWMGIINP
SGGSTSYAQKFQGRVTMTRDTSTSTVYMELSSLRSEDTAVYYCAKEGVADGYG
LVDVWGQGTMVTISS SEQ ID NO: 18 (HCVR of Antibody B)
QVQLVQSGAEVKKPGASVKVSCKASGYTFEGYYMHWVRQAPGQGLEWMGIIN
PEGGETSYAQKFQGRVTMTRDTSISTAYMELSRLRSDDTAVYYCAKEGVADGY
GLVDVWGQGTMVTVSS SEQ ID NO: 19 (HCVR of Antibody C)
QVQLVQSGAEVKKPGASVKVSCKASGYTFTAQYMHWVRQAPGQGLEWMGIIN
PSGGETGYAQKFQGRVTMTRDTSTSTVYMELSSLRSEDTAVYYCAKEGVADGY
GLVDVWGQGTMVTVSS SEQ ID NO: 20 (HCVR of Antibody D)
QVQLVQSGAEVKKPGASVKVSCKASGYTFEKYYMHWVRQAPGQGLEWMGIIN
PDGGSTGYAQKFQGRVTMTRDTSTSTVYMELSSLRSEDTAVYYCAKEGVADGY
GLVDVWGQGTMVTVSS SEQ ID NO: 21 (HCVR of Antibody E)
QVQLVQSGAEVKKPGASVKVSCKASGYTFTSNYMHWVRQAPGQGLEWMGIINP
SEGSTGYAQKFQGRVTMTRDTSTSTVYMELSSLRSEDTAVYYCAKEGVADGYG
LVDVWGQGTMVTVSS SEQ ID NO: 22 (HCVR of Antibody F)
QVQLVQSGAEVKKPGASVKVSCKASGYTFSAYYMHWVRQAPGQGLEWMIIHNP
DGGSTGYAQKFQGRVTMTRDTSTSTVYMELSSLRSEDTAVYYCAKEGVADGYG
LVDVWGQGTMVTVSS SEQ ID NO: 23 (LCVR of Antibody AF)
EIVLTQSPATLSLSPGERATLSCRASQSVSSYLAWYQQKPGQAPRLLIYDASKRAT
GIPARFSGSGSGTDFTLTISSLEPEDFAVYYCDQRNNWPLTFGGGTKVEIK SEQ ID NO: 24 (HC of Antibody A-S228P IgG4)
QVQLVQSGAEVKKPGASVKVSCKASGYTFTSYYMHWVRQAPGQGLEWMGIINP
SGGSTSYAQKFQGRVTMTRDTSTSTVYMELSSLRSEDTAVYYCAKEGVADGYG
LVDVWGQGTMVTISSASTKGPSVFPLAPCSRSTSESTAALGCLVKDYFPEPVTVS
WNSGALTSGVHTFPAVLQSSGLYSLSSVVTVPSSSLGTKTYTCNVDHKPSNTKVD
KRVESKYGPPCPPCPAPEFLGGPSVFLFPPKPKDTLMISRTPEVTCVVVDVSQEDP
EVQFNWYVDGVEVHNAKTKPREEQFNSTYRVVSVLTVLHQDWLNGKEYKCKV Amino Acid and Nucleotide Sequences SNKGLPSSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMHEALH
NHYTQKSTSLSLGK SEQ ID NO: 25 (HC of Antibody B S228P IgG4)
QVQLVQSGAEVKKPGASVKVSCKASGYTFEGYYMHWVRQAPGQGLEWMGIIN
PEGGETSYAQKFQGRVTMTRDTSISTAYMELSRLRSDDTAVYYCAKEGVADGY
GLVDVWGQGTMVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEAL
HNHYTQKSLSLSLGK SEQ ID NO: 26 (HC of Antibody C-S228P IgG4)
QVQLVQSGAEVKKPGASVKVSCKASGYTFTAQYMHWVRQAPGQGLEWMGIIN
PSGGETGYAQKFQGRVTMTRDTSTSTVYMELSSLRSEDTAVYYCAKEGVADGY
GLVDVWGQGTMVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEAL
HNHYTQKSLSLSLGK SEQ ID NO: 27 (EC of Antibody D-S228P IgG4)
QVQLVQSGAEVKKPGASVKVSCKASGYTFEKYYMHWVRQAPGQGLEWMGIIN
PDGGSTGYAQKFQGRVTMTRDTSTSTVYMELSSLRSEDTAVYYCAKEGVADGY
GLVDVWGQGTMVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEAL
HNHYTQKSLSLSLGK SEQ ID NO: 28 (HC of Antibody E-S228P IgG4)
QVQLVQSGAEVKKPGASVKVSCKASGYTFTSNYMHWVRQAPGQGLEWMGIINP
SEGSTGYAQKFQGRVTMTRDTSTSTVYMELSRSEDTAVYYCAKEGVADGYG
LVDVWGQGTMVTVSSASTKGPSVFPLAPCSRSTSESTAALGCLVKDYFPEPVTVS
WNSGALTSGVHTFPAVLQSSGLYSLSSVVTVPSSSLGTKTYTCNVDHKPSNTKVD
KRVESKYGPPCPPCPAPEFLGGPSVFLPPPKPKDTLMISRTPEVTCVVVDVSQEDP
EVQFNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMHEALH
NHYTQKSLSLSLGK SEQ ID NO: 29 (HC of Antibody F-S228P IgG4)
QVQLVQSGAEVKKPGASVKVSCKASGYTFSAYYMHWVRQAPGQGLEWMGIINP
DGGSTGYAQKFQGRVTMTRDTSTSTVYMELSSLRSEDTAVYYCAKEGVADGYG
LVDVWGQGTMVTVSSASTKGPSVFPLAPCSRSTSESTAALGCLVKDYYPEPVTVS
WNSGALTSGVHTFPAVLQSSGLYSLSSVVTVPSSSLGTKTYTCNVDHKPSNTKVD
KRVESKYGPPCPPCPAPEFLGGPSNTFLPPPKPKDTLMISRTPEVTCVVVDVSQEDP
EVQFNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMHEALH
NHYTQKSLSLSLGK SEQ ID NO: 30 (LC of Antibody A-F)
EIVLTQSPATLSLSPGERATLSCRASQSVSSYLAWYQQKPGQAPRLLIYDASKRAT
GIPARFSGSGSGTDFTLTISSLEPEDFAVYYCDQRNNWPLTFGGGTKVEIKRTVAA
PSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC SEQ ID NO: 31 (DNA of HC of Antibody A S228P IgG4)
CAGGTGCAGCTGGTGCAGTCTGGGGCTGAGGTGAAGAAGCCTGGGGCCTCAG
TGAAGGTTTCCTGCAAGGCATCTGGATACACCTTCACCAGCTACTATATGCAC
TGGGTGCGACAGGCCCCTGGACAAGGGCTTGAGTGGATGGGAATAATCAACC
CTAGTGGTGGTAGCACAAGCTACGCACAGAAGTTCCAGGGCAGAGTCACCAT
GACCAGGGACACGTCCACGAGCACAGTCTACATGGAGCTGAGCAGCCTGAGA
TCTGAGGACACGGCGGTGTACTACTGCGCCAAAGAGGGAGTGGCCGACGGAT
ATGGATTGGTAGACGTATGGGGTCAGGGTACAATGGTCACCATCTCCTCAGC
CAGCACCAAGGGACCCTCCGTGTTCCCTCTGGCTCCTTGCAGCAGGTCCACCA
GCGAATCCACCGCTGCCCTGGGCTGTCTGGTGAAAGACTACTTTCCCGAGCCT
GTGACCGTGAGCTGGAACTCCGGCGCTCTGACCAGCGGCGTGCACACATTTC
CTGCCGTGCTGCAGAGCTCCGGCCTGTACTCCCTGTCCTCCGTGGTGACAGTC

| Amino Acid and Nucleotide Sequences |
|---|
| CCCAGCAGCAGCCTGGGAACCAAGACCTACACCTGCAACGTCGACCACAAGC
CTTCCAACACCAAGGTGGACAAGAGGGTGGAGTCCAAATATGGCCCCCCCTG
CCCTCCTTGTCCCGCTCCTGAGTTCCTGGGCGGCCCTTCCGTGTTCCTGTTCCC
TCCCAAGCCCAAGGACACCCTGATGATCTCCCGGACCCCCGAGGTGACCTGT
GTGGTGGTGGACGTGTCCCAGGAGGACCCTGAGGTGCAATTCAACTGGTACG
TGGACGGCGTCGAGGTGCACAACGCCAAGACCAAGCCCCGGGAGGAGAGT
TCAACAGCACCTACCGGGTCGTGTCCGTGCTGACCGTGCTGCACCAGGATTGG
CTCAACGGCAAGGAGTACAAGTGCAAAGTGTCCAATAAGGGCCTGCCCTCCT
CCATCGAGAAGACCATCTCCAAGGCCAAGGGACAACCCCGTGAGCCCCAGGT
GTACACCCTGCCTCCTTCCCAGGAGGAGATGACCAAGAATCAGGTGTCCCTC
ACCTGCCTGGTGAAGGGCTTCTACCCTTCCGACATCGCCGTGGAATGGGAGTC
CAACGGCCAGCCCGAGAACAACTACAAGACAACCCCCCCTGTCCTGGACAGC
GACGGCTCCTTCTTTCTGTACAGCAGGCTGACCGTGGACAAGAGCCGGTGGC
AGGAGGGCAACGTGTTTAGCTGTAGCGTCATGCACGAGGCCCTGCACAACCA
CTACACCCAGAAATCCCTGTCCCTGTCCCTGGGCAAGTGATGA SEQ ID NO: 32 (DNA of HC of Antibody B S228P IgG4)
CAGGTGCAGCTGGTGCAGTCTGGGGCTGAGGTGAAGAAGCCTGGGGCCTCAG
TGAAGGTTTCCTGCAAGGCATCTGGATACACCTTCGAGGGTTACTATATGCAC
TGGGTGCGACAGGCCCCTGGACAAGGGCTTGAGTGGATGGGAATAATCAACC
CTGAGGGTGGTGAGACAAGCTACGCACAGAAGTTCCAGGGCAGAGTCACCAT
GACCAGGGACACGTCCATCAGCACAGCCTACATGGAGCTGAGCAGGCTGAGA
TCTGACGACACGGCGGTGTACTACTGCGCCAAAGAGGGAGTGGCCGACGGAT
ATGGATTGGTAGACGTATGGGGTCAGGGTACAATGGTCACCGTCTCCTCAGC
CAGCACCAAGGGACCCTCCGTGTTCCCTCTGGCTCCTTGCAGCAGGTCCACCA
GCGAATCCACCGCTGCCCTGGGCTGTCTGGTGAAAGACTACTTTCCCGAGCCT
GTGACCGTGAGCTGGAACTCCGGCGCTCTGACCAGCGGCGTGCACACATTTC
CTGCCGTGCTGCAGAGCTCCGGCCTGTACTCCCTGTCCTCCGTGGTGACAGTC
CCCAGCAGCAGCCTGGGAACCAAGACCTACACCTGCAACGTCGACCACAAGC
CTTCCAACACCAAGGTGGACAAGAGGGTGGAGTCCAAATATGGCCCCCCCTG
CCCTCCTTGTCCCGCTCCTGAGTTCCTGGGCGGCCCTTCCGTGTTCCTGTTCCC
TCCCAAGCCCAAGGACACCCTGATGATCTCCCGGACCCCCGAGGTGACCTGT
GTGGTGGTGGACGTGTCCCAGGAGGACCCTGAGGTGCAATTCAACTGGTACG
TGGACGGCGTCGAGGTGCACAACGCCAAGACCAAGCCCCGGGAGGAGCAGT
TCAACAGCACCTACCGGGTCGTGTCCGTGCTGACCGTGCTGCACCAGGATTGG
CTCAACGGCAAGGAGTACAAGTGCAAAGTGTCCAATAAGGGCCTGCCCTCCT
CCATCGAGAAGACCATCTCCAAGGCCAAGGGACAACCCCGTGAGCCCCAGGT
GTACACCCTGCCTCCTTCCCAGGAGGAGATGACCAAGAATCAGGTGTCCCTC
ACCTTGCCTGGTGAAGGGCTTCTACCCTTCCGACATCGCCGTGGAATGGGAGTC
CAACGGCCAGCCCGAGAACAACTACAAGACAACCCCCCCTGTCCTGGACAGC
GACGGCTCCTTCTTTCTGTACAGCAGGCTGACCGTGGACAAGAGCCGGTGGC
AGGAGGGCAACGTGTTTAGCTGTAGCGTCATGCACGAGGCCCTGCACAACCA
CTACACCCAGAAATCCCTGTCCCTGTCCCTGGGCAAGTGATGA SEQ ID NO: 33 (DNA of HC of Antibody C S228P IgG4)
CAGGTGCAGCTGGTGCAGTCTGGGGCTGAGGTGAAGAAGCCTGGGGCCTCAG
TGAAGGTTTCCTGCAAGGCATCTGGATACACCTTCACCGCTCAGTATATGCAC
TGGGTGCGACAGGCCCCTGGACAAGGGCTTGAGTGGATGGGAATAATCAACC
CTAGTGGTGGTGAGACAGGGTACGCACAGAAGTTCCAGGGCAGAGTCACCAT
GACCAGGGACACGTCCACGAGCACACTTCTACATGGAGCTGAGCAGCCTGAGA
TCTGAGGACACGGCGGTGTACTACTGCGCCAAAGAGGGAGTGGCCGACGGAT
ATGGATTGGTAGACGTATGGGGTCAGGGTACAATGGTCACCGTCTCCTCAGC
CAGCACCAAGGCTACCCTCCGTGTTCCCTCTGGCTCCTTGCAGCAGGTCCACCA
GCGAATCCACCGCTGCCCTGGGCTGTCTGGTGAAAGACTACTTTCCCGAGCCT
GTGACCGTGAGCTGGAACTCCGGCGCTCTGACCAGCGGCGTGCACACATTTC
CTGCCGTGCTGCAGAGCTCCGGCCTGTACTCCCTGTCCTCCGTGGTGACAGTC
CCCAGCAGCAGCCTGGGAACCAAGACCTACACCTGCAACGTCGACCACAAGC
CTTCCAACACCAAGGTGGACAAGAGGGTGGAGTCCAAATATGGCCCCCCCTG
CCCTCCTTGTCCCGCTCCTGAGTTCCTGGGCGGCCCTTCCGTGTTCCTGTTCCC
TCCCAAGCCCAAGGACACCCTGATGATCTCCCGGACCCCCGAGGTGACCTGT
GTGGTGGTGGACGTGTCCCAGGAGGACCCTGAGGTGCAATTCAACTGGTACG
TGGACGGCGTCGAGGTGCACAACGCCAAGACCAAGCCCCGGGAGGAGCAGT
TCAACAGCACCTACCGGGTCGTGTCCGTGCTGACCGTGCTGCACCAGGATTGG
CTCAACGGCAAGGAGTACAAGTGCAAAGTGTCCAATAAGGGCCTGCCCTCCT
CCATCGAGAAGACCATCTCCAAGGCCAAGGGACAACCCCGTGAGCCCCAGGT
GTACACCCTGCCTCCTTCCCAGGAGGAGATGACCAAGAATCAGGTGTCCCrC
ACCTGCCTGGTGAAGGGCTTCTACCCTTCCGACATCGCCGTGGAATGGGAGTC
CAACGGCCAGCCCGAGAACAACTACAAGACAACCCCCCCTGTCCTGGACAGC
GACGGCTCCTTCTTTCTGTACAGCAGGCTGACCGTGGACAAGAGCCGGTGGC
AGGAGGGCAACGTGTTTAGCTGTAGCGTCATGCACGAGGCCCTGCACAACCA
CTACACCCAGAAATCCCTGTCCCTGTCCCTGGGCAAGTGATGA SEQ ID NO: 34 (DNA of HC of Antibody D S228P IgG4)
CAGGTGCAGCTGGTGCAGTCTGGGGCTGAGGTGAAGAAGCCTGGGGCCTCAG
TGAAGGTTTCCTGCAAGGCATCTGGATACACCTTCGAGAAGTACTATATGCAC
TGGGTGCGACAGGCCCCTGGACAAGGGCTTGAGTGGATGGGAATAATCAACC
CTGATGGTGGTAGCACAGGGTACGCACAGAAGTTCCAGGGCAGAGTCACCAT |

| Amino Acid and Nucleotide Sequences |
| --- |
| GACCAGGGACACGTCCACGAGCACAGTCTACATGGAGCTGAGCAGCCTGAGA |
| TCTGAGGACACGGCGGTGTACTACTGCGCCAAAGAGGGAGTGGCCGACGGAT |
| ATGGATTGGTAGACGTATGGGGTCAGGGTACAATGGTCACCGTCTCCTCAGC |
| CAGCACCAAGGGACCCTCCGTGTTCCCTCTGGCTCCTTGCAGCAGGTCCACCA |
| GCGAATCCACCGCTGCCCTGGGCTGTCTGGTGAAAGACTACTTTCCCGAGCCT |
| GTGACCGTGAGCTGGAACTCCGGCGCTCTGACCAGCGGCGTGCACACATTTC |
| CTGCCGTGCTGCAGAGCTCCGGCCTGTACTCCCTGTCCTCCGTGGTGACAGTC |
| CCCAGCAGCAGCCTGGGAACCAAGACCTACACCTGCAACGTCGACCACAAGC |
| CTTCCAACACCAAGGTGGACAAGAGGGTGGAGTCCAAATATGGCCCCCCCTG |
| CCCTCCTTGTCCCGCTCCTGAGTTCCTGGGCGGCCCTTCCGTGTTCCTGTTCCC |
| TCCCAAGCCCAAGGACACCCTGATGATCTCCCGGACCCCCGAGGTGACCTGT |
| GTGGTGGTGGACGTGTCCCAGGAGGACCCTGAGGTGCAATTCAACTGGTACG |
| TGGACGGCGTCGAGGTGCACAACGCCAAGACCAAGCCCGGGAGGAGCAGT |
| TCAACAGCACCTACCGGGTCGTGTCCGTGCTGACCGTGCTGCACCAGGATTGG |
| CTCAACGGCAAGGAGTACAAGTGCAAAGTGTCCAATAAGGGCCTGCCCTCCT |
| CCATCGAGAAGACCATCTCCAAGGCCAAGGGACAACCCCGTGAGCCCCAGGT |
| GTACACCCTGCCTCCTTCCCAGGAGGAGATGACCAAGAATCAGGTGTCCCTC |
| ACCTGCCTGGTGAAGGGCTTCTACCCTTCCGACATCGCCGTGGAATGGGAGTC |
| CAACGGCCAGCCCGAGAACAACTACAAGACAACCCCCCCTGTCCTGGACAGC |
| GACGGCTCCTTCTTTCTGTACAGCAGGCTGACCGTGGACAAGAGCCGGTGGC |
| AGGAGGGCAACGTGTTTAGCTGTAGCGTCATGCACGAGGCCCTGCACAACCA |
| CTACACCCAGAAATCCCTGTCCCTGTCCCTGGGCAAGTGATGA |

SEQ ID NO: 35 (DNA of HC of Antibody E S228P IgG4)
CAGGTGCAGCTGGTGCAGTCTGGGGCTGAGGTGAAGAAGCCTGCGGCCTCAG
TGAAGGTTTCCTGCAAGGCATCTGGATACACCTTCACCAGCAATTATATGCAC
TGGGTGCGACAGGCCCCTGGACAAGGGCTTGAGTGGATGGGAATAATCAACC
CTAGTGAGGGTAGCACAGGTTACGCACAGAAGTTCCAGGGCAGAGTCACCAT
GACCAGGGACACGTCCACGAGCACAGTCTACATGGAGCTGAGCAGCCTGAGA
TCTGAGGACACGGCGGTGTACTACTGCGCCAAAGAGGGAGTGGCCGACGGAT
ATGGATTGGTAGACGTATGGGGTCAGGGTACAATGGTCACCGTCTCCTCAGC
CAGCACCAAGGGACCCTCCGTGTTCCCTCTGGCTCCTTGCAGCAGGTCCACCA
GCGAATCCACCGCTGCCCTGGGCTGTCTGGTGAAAGACTACTTTCCCGAGCCT
GTGACCGTGAGCTGGAACTCCGGCGCTCTGACCAGCGGCGTGCACACATTTC
CTGCCGTGCTGCAGAGCTCCGGCCTGTACTCCCTGTCCTCCGTGGTGACAGTC
CCCAGCAGCAGCCTGGGAACCAAGACCTACACCTGCAACGTCGACCACAAGC
CTTCCAACACCAAGGTGGACAAGAGGGTGGAGTCCAAATATGGCCCCCCCTG
CCCTCCTTGTCCCGCTCCTGAGTTCCTGGGCGGCCCTTCCGTGTTCCTGTTCCC
TCCCAAGCCCAAGGACACCCTGATGATCTCCCGGACCCCCGAGGTGACCTGT
GTGGTGGTGGACGTGTCCCAGGAGGACCCTGAGGTGCAATTCAACTGGTACG
TGGACGGCGTCGAGGTGCACAACGCCAAGACCAAGCCCGGGAGGAGCAGT
TCAACAGCACCTACCGGGTCGTGTCCGTGCTGACCGTGCTGCACCAGGATTGG
CTCAACGGCAAGGAGTACAAGTGCAAAGTGTCCAATAAGGGCCTGCCCTCCT
CCATCGAGAAGACCATCTCCAAGGCCAAGGGACAACCCCGTGAGCCCCAGGT
GTACACCCTGCCTCCTTCCCAGGAGGAGATGACCAAGAATCAGGTGTCCCTC
ACCTGCCTGGTGAAGGGCTTCTACCCTTCCGACATCGCCGTGGAATGGGAGTC
CAACGGCCAGCCCGAGAACAACTACAAGACAACCCCCCCTGTCCTGGACAGC
GACGGCTCCTTCTTTCTGTACAGCAGGCTGACCGTGGACAAGAGCCGGTGGC
AGGAGGGCAACGTGTTTAGCTGTAGCGTCATGCACGAGGCCCTGCACAACCA
CTACACCCAGAAATCCCTGTCCCTGTCCCTGGGCAAGTGATGA SEQ ID NO: 36 (DNA of HC of Antibody F S228P IgG4)
CAGGTGCAGCTGGTGCAGTCTGGGGCTGAGGTGAAGAAGCCTGGGGCCTCAG
TGAAGGTTTCCTGCAAGGCATCTGGATACACCTTCAGTGCGTACTATATGCAC
TGGGTGCGACAGGCCCCTGGACAAGGGCTTGAGTGGATGGGAATAATCAACC
CTGATGGTGGTAGCACAGGGTACGCACAGAAGTTCCAGGGCAGAGTCACCAT
GACCAGGGACACGTCCACGAGCACAGTCTACATGGAGCTGAGCAGCCTGAGA
TCTGAGGACACGGCGGTGTACTACTGCGCCAAAGAGGGAGTGGCCGACGGAT
ATGGATTGGTAGACGTATGGGGTCAGGGTACAATGGTCACCGTCTCCTCAGC
CAGCACCAAGGGACCCTCCGTGTTCCCTCTGGCTCCTTGCAGCAGGTCCACCA
GCGAATCCACCGCTGCCCTGGGCTGTCTGGTGAAAGACTACTTTCCCGAGCCT
GTGACCGTGAGCTGGAACTCCGGCGCTCTGACCAGCGGCGTGCACACATTTC
CTGCCGTGCTGCAGAGCTCCGGCCTGTACTCCCTGTCCTCCGTGGTGACAGTC
CCCAGCAGCAGCCTGGGAACCAAGACCTACACCTGCAACGTCGACCACAAGC
CTTCCAACACCAAGGTGGACAAGAGGGTGGAGTCCAAATATGGCCCCCCCTG
CCCTCCTTGTCCCGCTCCTGAGTTCCTGGGCGGCCCTTCCGTGTTCCTGTTCCC
TCCCAAGCCCAAGGACACCCTGATGATCTCCCGGACCCCCGAGGTGACCTGT
GTGGTGGTGGACGTGTCCCAGGAGGACCCTGAGGTGCAATTCAACTGGTACG
TGGACGGCGTCGAGGTGCACAACGCCAAGACCAAGCCCGGGAGGAGCAGT
TCAACAGCACCTACCGGGTCGTGTCCGTGCTGACCGTGCTGCACCAGGATTGG
CTCAACGGCAAGGAGTACAAGTGCAAAGTGTCCAATAAGGGCCTGCCCTCCT
CCATCGAGAAGACCATCTCCAAGGCCAAGGGACAACCCCGTGAGCCCCAGGT
GTACACCCTGCCTCCTTCCCAGGAGGAGATGACCAAGAATCAGGTGTCCCTC
ACCTGCCTGGTGAAGGGCTTCTACCCTTCCGACATCGCCGTGGAATGGGAGTC

| Amino Acid and Nucleotide Sequences |
|---|
| CAACGGCCAGCCCGAGAACAACTACAAGACAACCCCCCCTGTCCTGGACAGC<br>GACGGCTCCTTCTTTCTGTACAGCAGGCTGACCGTGGACAAGAGCCGGTGGC<br>AGGAGGGCAACGTGTTTAGCTGTAGCGTCATGCACGAGGCCCTGCACAACCA<br>CTACACCCAGAAATCCCTGTCCCTGTCCCTGGGCAAGTGATGA<br><br>SEQ ID NO: 37 (DNA of HC of Antibody C and E)<br>GAAATTGTGTTGACACAGTCTCCAGCCACCCTGTCTTTGTCTCCAGGGGAAAG<br>AGCCACCCTCTCCTGCAGGGCCAGTCAGAGTGTTAGCAGCTACTTAGCCTGGT<br>ACCAACAGAAACCTGGCCAGGCTCCCAGGCTCCTCATCTATGATGCATCCAA<br>AAGGGCCACTGGCATCCCAGCCAGGTTCAGTGGCAGTGGGTCTGGGACAGAC<br>TTCACTCTCACCATCAGCAGCCTAGAGCCTGAAGATTTTGCAGTTTATTACTG<br>TGACCAGAGAAACAATTGGCCTCTCACTTTTGGCGGAGGGACCAAGGTTGAG<br>ATCAAACGGACCGTGGCTGCCCCTAGCGTGTTCATCTTCCCTCCCTCCGATGA<br>GCAGCICAAGTCCGGCACAGCCAGCGTGGTGTGCCTGCTGAATAACTTCTACC<br>CCCGGGAGGCCAAAGTGGAGTGGAAGGTGGACAACGCTCTGCAGTCCGGCAA<br>TTCCAGGAGAGCGTCACCGAGCAGGACAGCAAGGACAGCACCTACTCCCTG<br>AGCTCCACCCTGACCCTGAGCAAGGCCGACTACGAGAAGCACAAGGTCTACG<br>CCTGCGAGGTCACCCATCAGGGCCTGTCCAGCCCCGTGACCAAGTCCTTCAAC<br>CGGGGCGAGTGCTGATGA<br><br>SEQ ID NO: 38 (mouse PD-1)<br>MWVRQVPWSFTWAVLQLSWQSGWLLEVPNGPWRSLTFYPAWLTVSEGANATF<br>TCSLSNWSEDLMLNWNRLSPSNQTEKQAAFCNGLSQPVQDARFQIIQLPNRHDF<br>HMNILDTRRNDSGIYLCGAISLHPKAKIEESPGAELVVTERILETSTRYPSPSPKPE<br>GRFQGMYIGIMSALVGIPVLLLLAWALAVFCSTSMSEARGAGSKDDTLKEEPSAA<br>PVPSVAYEELDFQGREKTPELPTACVHTEYATIVFTEGLGASAMGRRGSADGLQG<br>PRPPRHEDGHCSWPL |

We claim:

1. An antibody that binds human PD-1 (SEQ ID NO: 1), comprising a light chain (LC) and a heavy chain (HC), wherein the light chain comprises light chain complementarity determining regions LCDR1, LCDR2, and LCDR3, and wherein the heavy chain comprises heavy chain complementarity determining regions HCDR1, HCDR2, and HCDR3, wherein (i) LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and HCDR1, HCDR2, and HCDR3 consist of the amino acid sequences KASGYTFTSYYMH (SEQ ID NO: 2), IINPSGGSTSYAQKFQG (SEQ ID NO: 8), and AKEGVADGYGLVDV (SEQ ID NO: 13), respectively;

(ii) LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and HCDR1, HCDR2, and HCDR3 consist of the amino acid sequences KASGYTFEGYYMH (SEQ ID NO: 3), IINPEGGETSYAQKFQG (SEQ ID NO: 9), and AKEGVADGYGLVDV (SEQ ID NO: 13), respectively;

(iii) LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and HCDR1, HCDR2, and HCDR3 consist of the amino acid sequences KASGYTFTAQYMH (SEQ ID NO: 4), IINPSGGFTGYAQKFQG (SEQ ID NO: 10), and AKEGVADGYGLVDV (SEQ ID NO: 13), respectively;

(iv) LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and HCDR1, HCDR2, and HCDR3 consist of the amino acid sequences KASGYTFEKYYMH (SEQ ID NO: 5), IINPDGGSTGYAQKFQG (SEQ ID NO: 12), and AKEGVADGYGLVDV (SEQ ID NO: 13), respectively;

(v) LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and HCDR1, HCDR2, and HCDR3 consist of the amino acid sequences KASGYTFTSNYMH (SEQ ID NO: 6), IINPSEGSTGYAQKFQG (SEQ ID NO: 11), and AKEGVADGYGLVDV (SEQ ID NO: 13), respectively; or (vi) LCDR1, LCDR2, and LCDR3 consist of the amino acid sequences RASQSVSSYLA (SEQ ID NO: 14), YDASKRAT (SEQ ID NO: 15), and DQRNNWPLT (SEQ ID NO: 16), respectively, and HCDR1, HCDR2, and HCDR3 consist of the amino acid sequences KASGYTFSAYYMH (SEQ ID NO: 7), IINPDGGSTGYAQKFQG (SEQ ID NO: 12), and AKEGVADGYGLVDV (SEQ ID NO: 13), respectively.

2. An antibody, comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 23, and the HCVR has the amino acid sequence given in SEQ ID NO: 17, SEQ ID NO: 18, SEQ ID NO: 19, SEQ ID NO: 20, SEQ ID NO: 21, or SEQ ID NO: 22.

3. The antibody of claim 2, wherein the LC has the amino acid sequence given in SEQ ID NO: 30, and the HC has the amino acid sequence given in SEQ ID NO: 24, SEQ ID NO: 25, SEQ ID NO: 26, SEQ ID NO: 27, SEQ ID NO: 28, or SEQ ID NO: 29.

4. The antibody of claim 3, comprising two light chains and two heavy chains, wherein each light chain has the amino acid sequence given in SEQ ID NO: 30, and each heavy chain has the amino acid sequence given in SEQ ID NO: 24, SEQ ID NO: 25, SEQ ID NO: 26, SEQ ID NO: 27, SEQ ID NO: 28, or SEQ ID NO: 29.

5. The antibody of claim 4, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

6. The antibody of claim 1, wherein the antibody is glycosylated.

7. A pharmaceutical composition, comprising the antibody of claim 1, and an acceptable carrier, diluent, or excipient.

8. A method of treating cancer, comprising administering to a patient in need thereof, an effective amount of the antibody of claim 1.

9. The method of claim 8, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

10. The method of claim 8, further comprising administering simultaneously, separately, or sequentially one or more anti-tumor agents.

11. The combination for use of claim 10, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

12. A pharmaceutical composition, comprising the antibody of claim 2, and an acceptable carrier, diluent, or excipient.

13. A method of treating cancer, comprising administering to a patient in need thereof, an effective amount of the antibody of claim 2.

14. The method of claim 13, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

15. The method of claim 13, further comprising administering simultaneously, separately, or sequentially one or more anti-tumor agents.

16. The method of claim 15, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

* * * * *

```
                           SEQUENCE LISTING

<160> NUMBER OF SEQ ID NOS: 38

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
```

```
                180                 185                 190
Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Lys Ala Ser Gly Tyr Thr Phe Thr Ser Tyr Tyr Met His
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Lys Ala Ser Gly Tyr Thr Phe Glu Gly Tyr Tyr Met His
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic Construct

<400> SEQUENCE: 4

Lys Ala Ser Gly Tyr Thr Phe Thr Ala Gln Tyr Met His
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Lys Ala Ser Gly Tyr Thr Phe Glu Lys Tyr Tyr Met His
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Construct
```

```
<400> SEQUENCE: 6

Lys Ala Ser Gly Tyr Thr Phe Thr Ser Asn Tyr Met His
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic Construct

<400> SEQUENCE: 7

Lys Ala Ser Gly Tyr Thr Phe Ser Ala Tyr Tyr Met His
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Ile Ile Asn Pro Ser Gly Gly Ser Thr Ser Tyr Ala Gln Lys Phe Gln
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

Ile Ile Asn Pro Glu Gly Gly Glu Thr Ser Tyr Ala Gln Lys Phe Gln
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Ile Ile Asn Pro Ser Gly Gly Glu Thr Gly Tyr Ala Gln Lys Phe Gln
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Ile Ile Asn Pro Ser Glu Gly Ser Thr Gly Tyr Ala Gln Lys Phe Gln
1               5                   10                  15

Gly
```

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Ile Ile Asn Pro Asp Gly Gly Ser Thr Gly Tyr Ala Gln Lys Phe Gln
1               5                   10                  15

Gly

<210> SEQ ID NO 13
<211> LENGTH: 14
<212> TYPE: PRT
<213> ORGANISM: Artificial Sequence
<220> FEATURE:
<223> OTHER INFORMATION: Synthetic Construct

<400> SEQUENCE: 13

Ala Lys Glu Gly Val Ala Asp Gly Tyr Gly Leu Val Asp Val
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Arg Ala Ser Gln Ser Val Ser Ser Tyr Leu Ala
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Tyr Asp Ala Ser Lys Arg Ala Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Asp Gln Arg Asn Asn Trp Pro Leu Thr
1               5

<210> SEQ ID NO 17
<211> LENGTH: 121
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Glu Gly Val Ala Asp Gly Tyr Gly Leu Val Asp Val Trp Gly
            100                 105                 110

Gln Gly Thr Met Val Thr Ile Ser Ser
            115                 120

<210> SEQ ID NO 18
<211> LENGTH: 121
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Gly Tyr
            20                  25                  30

Tyr Met His Trp Val Arg Gln Ala Pro Gly Gln Gly Leu Glu Trp Met
        35                  40                  45

Gly Ile Ile Asn Pro Glu Gly Gly Glu Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Glu Gly Val Ala Asp Gly Tyr Gly Leu Val Asp Val Trp Gly
            100                 105                 110

Gln Gly Thr Met Val Thr Val Ser Ser
            115                 120

<210> SEQ ID NO 19
<211> LENGTH: 121
<212> TYPE: PRT
<213> ORGANISM: Artificial Sequence
<220> FEATURE:
<223> OTHER INFORMATION: Synthetic Construct

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Gln
            20                  25                  30

Tyr Met His Trp Val Arg Gln Ala Pro Gly Gln Gly Leu Glu Trp Met
        35                  40                  45

Gly Ile Ile Asn Pro Ser Gly Gly Glu Thr Gly Tyr Ala Gln Lys Phe
    50                  55                  60

Gln Gly Arg Val Thr Met Thr Arg Asp Thr Ser Thr Ser Thr Val Tyr

```
                65                  70                  75                  80
Met Glu Leu Ser Ser Leu Arg Ser Glu Asp Thr Ala Val Tyr Tyr Cys
                85                  90                  95

Ala Lys Glu Gly Val Ala Asp Gly Tyr Gly Leu Val Asp Val Trp Gly
            100                 105                 110

Gln Gly Thr Met Val Thr Val Ser Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: Synthetic Construct

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Lys Tyr
            20                  25                  30

Tyr Met His Trp Val Arg Gln Ala Pro Gly Gln Gly Leu Glu Trp Met
        35                  40                  45

Gly Ile Ile Asn Pro Asp Gly Gly Ser Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Glu Gly Val Ala Asp Gly Tyr Gly Leu Val Asp Val Trp Gly
            100                 105                 110

Gln Gly Thr Met Val Thr Val Ser Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Tyr Met His Trp Val Arg Gln Ala Pro Gly Gln Gly Leu Glu Trp Met
        35                  40                  45

Gly Ile Ile Asn Pro Ser Glu Gly Ser Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Glu Gly Val Ala Asp Gly Tyr Gly Leu Val Asp Val Trp Gly
            100                 105                 110

Gln Gly Thr Met Val Thr Val Ser Ser
        115                 120
```

```
<210> SEQ ID NO 22
<211> LENGTH: 121
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
                20                  25                  30

Tyr Met His Trp Val Arg Gln Ala Pro Gly Gln Gly Leu Glu Trp Met
            35                  40                  45

Gly Ile Ile Asn Pro Asp Gly Gly Ser Thr Gly Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Glu Gly Val Ala Asp Gly Tyr Gly Leu Val Asp Val Trp Gly
            100                 105                 110

Gln Gly Thr Met Val Thr Val Ser Ser
        115                 120

<210> SEQ ID NO 23
<211> LENGTH: 107
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Asp Gln Arg Asn Asn Trp Pro Leu
                85                  90                  95

Thr Phe Gly Gly Gly Thr Lys Val Glu Ile Lys
            100                 105

<210> SEQ ID NO 24
<211> LENGTH: 448
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
            20                  25                  30
Tyr Met His Trp Val Arg Gln Ala Pro Gly Gln Gly Leu Glu Trp Met
             35                  40                  45
Gly Ile Ile Asn Pro Ser Gly Gly Ser Thr Ser Tyr Ala Gln Lys Phe
             50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Lys Glu Gly Val Ala Asp Gly Tyr Gly Leu Val Asp Val Trp Gly
                100                 105                 110
Gln Gly Thr Met Val Thr Ile Ser Ser Ala Ser Thr Lys Gly Pro Ser
                115                 120                 125
Val Phe Pro Leu Ala Pro Cys Ser Arg Ser Thr Ser Glu Ser Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Lys Thr Tyr Thr Cys Asn Val Asp His
                195                 200                 205
Lys Pro Ser Asn Thr Lys Val Asp Lys Arg Val Glu Ser Lys Tyr Gly
                210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
                260                 265                 270
Glu Val Gln Phe Asn Trp Tyr Val Asp Gly Val Glu Val His Asn Ala
                275                 280                 285
Lys Thr Lys Pro Arg Glu Glu Gln Phe Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Gln Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
                420                 425                 430
Leu His Asn His Tyr Thr Gln Lys Ser Leu Ser Leu Ser Leu Gly Lys
                435                 440                 445
```

<210> SEQ ID NO 25
<211> LENGTH: 448
<212> TYPE: PRT
<213> ORGANISM: Artificial Sequence
<220> FEATURE:
<223> OTHER INFORMATION: Synthetic Construct

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Gly Tyr
            20                  25                  30

Tyr Met His Trp Val Arg Gln Ala Pro Gly Gln Gly Leu Glu Trp Met
        35                  40                  45

Gly Ile Ile Asn Pro Glu Gly Gly Glu Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Glu Gly Val Ala Asp Gly Tyr Gly Leu Val Asp Val Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365
```

```
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
                420                 425                 430
Leu His Asn His Tyr Thr Gln Lys Ser Leu Ser Leu Ser Leu Gly Lys
            435                 440                 445
```

<210> SEQ ID NO 26
<211> LENGTH: 448
<212> TYPE: PRT
<213> ORGANISM: Artificial Sequence
<220> FEATURE:
<223> OTHER INFORMATION: Synthetic Construct

<400> SEQUENCE: 26

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ala Gln
            20                  25                  30
Tyr Met His Trp Val Arg Gln Ala Pro Gly Gln Gly Leu Glu Trp Met
        35                  40                  45
Gly Ile Ile Asn Pro Ser Gly Gly Glu Thr Gly Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Lys Glu Gly Val Ala Asp Gly Tyr Gly Leu Val Asp Val Trp Gly
            100                 105                 110
Gln Gly Thr Met Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
```

-continued

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
            435                 440                 445

<210> SEQ ID NO 27
<211> LENGTH: 448
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Lys Tyr
                20                  25                  30

Tyr Met His Trp Val Arg Gln Ala Pro Gly Gln Gly Leu Glu Trp Met
            35                  40                  45

Gly Ile Ile Asn Pro Asp Gly Gly Ser Thr Gly Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Glu Gly Val Ala Asp Gly Tyr Gly Leu Val Asp Val Trp Gly
                100                 105                 110

Gln Gly Thr Met Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

-continued

```
Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 28
<211> LENGTH: 448
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Tyr Met His Trp Val Arg Gln Ala Pro Gly Gln Gly Leu Glu Trp Met
        35                  40                  45

Gly Ile Ile Asn Pro Ser Glu Gly Ser Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Glu Gly Val Ala Asp Gly Tyr Gly Leu Val Asp Val Trp Gly
            100                 105                 110

Gln Gly Thr Met Val Thr Val Ser Ser Ala Ser Thr Lys Gly Pro Ser
        115                 120                 125
```

```
Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 29
<211> LENGTH: 448
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
                20                  25                  30

Tyr Met His Trp Val Arg Gln Ala Pro Gly Gln Gly Leu Glu Trp Met
                35                  40                  45
```

Gly Ile Ile Asn Pro Asp Gly Ser Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Glu Gly Val Ala Asp Gly Tyr Gly Leu Val Asp Val Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 30
<211> LENGTH: 214

<212> TYPE: PRT
<213> ORGANISM: Artificial Sequence
<220> FEATURE:
<223> OTHER INFORMATION: Synthetic Construct

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Asp Gln Arg Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 31
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg atgggaata atcaaccta gtggtggtag cacaagctac        180
gcacagaagt tccagggcag agtcaccatg accaggaca cgtccacgag cacagtctac     240
atggagctga gcagcctgag atctgaggac acggcggtgt actactgcgc aaagaggga     300 gtggccgacg gatatggatt ggtagacgta tggggtcagg gtacaatggt caccatctcc     360
tcagccagca ccaagggacc ctccgtgttc cctctggctc cttgcagcag gtccaccagc     420
gaatccaccg ctgccctggg ctgtctggtg aaagactact ttcccgagcc tgtgaccgtg     480
agctggaact ccgcgctct gaccagcggc gtgcacacat tcctgccgt gctgcagagc      540 tccggcctgt actccctgtc ctccgtggtg acagtcccca gcagcagcct gggaaccaag     600

| | |
|---|---|
| acctacacct gcaacgtcga ccacaagcct tccaacacca aggtggacaa gagggtggag | 660 |
| tccaaatatg gccccccctg ccctccttgt cccgctcctg agttcctggg cggcccttcc | 720 |
| gtgttcctgt tccctcccaa gcccaaggac accctgatga tctcccggac ccccgaggtg | 780 |
| acctgtgtgg tggtggacgt gtcccaggag gaccctgagg tgcaattcaa ctggtacgtg | 840 |
| gacggcgtcg aggtgcacaa cgccaagacc aagccccggg aggagcagtt caacagcacc | 900 |
| taccgggtcg tgtccgtgct gaccgtgctg caccaggatt ggctcaacgg caaggagtac | 960 |
| aagtgcaaag tgtccaataa gggcctgccc tcctccatcg agaagaccat ctccaaggcc | 1020 |
| aagggacaac cccgtgagcc ccaggtgtac accctgcctc cttcccagga ggagatgacc | 1080 |
| aagaatcagg tgtccctcac ctgcctggtg aagggcttct acccttccga catcgccgtg | 1140 |
| gaatgggagt ccaacggcca gcccgagaac aactacaaga caaccccccc tgtcctggac | 1200 |
| agcgacggct ccttctttct gtacagcagg ctgaccgtgg acaagagccg gtggcaggag | 1260 |
| ggcaacgtgt ttagctgtag cgtcatgcac gaggccctgc acaaccacta cacccagaaa | 1320 |
| tccctgtccc tgtccctggg caagtgatga | 1350 |

<210> SEQ ID NO 32
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 32

| | |
|---|---|
| caggtgcagc tggtgcagtc tggggctgag gtgaagaagc ctggggcctc agtgaaggtt | 60 |
| tcctgcaagg catctggata caccttcgag ggttactata tgcactgggt gcgacaggcc | 120 |
| cctggacaag gcttgagtg gatgggaata atcaaccctg agggtggtga gacaagctac | 180 |
| gcacagaagt tccagggcag agtcaccatg accagggaca cgtccatcag cacagcctac | 240 |
| atggagctga gcaggctgag atctgacgac acggcgtgt actactgcgc caaagaggga | 300 |
| gtggccgacg gatatggatt ggtagacgta tggggtcagg gtacaatggt caccgtctcc | 360 |
| tcagccagca ccaagggacc ctccgtgttc cctctggctc cttgcagcag gtccaccagc | 420 |
| gaatccaccg ctgccctggg ctgtctggtg aaagactact tcccgagcc tgtgaccgtg | 480 |
| agctggaact ccggcgctct gaccagcggc gtgcacacat tcctgccgt gctgcagagc | 540 |
| tccggcctgt actccctgtc ctccgtggtg acagtcccca gcagcagcct gggaaccaag | 600 |
| acctacacct gcaacgtcga ccacaagcct tccaacacca aggtggacaa gagggtggag | 660 |
| tccaaatatg gccccccctg ccctccttgt cccgctcctg agttcctggg cggcccttcc | 720 |
| gtgttcctgt tccctcccaa gcccaaggac accctgatga tctcccggac ccccgaggtg | 780 |
| acctgtgtgg tggtggacgt gtcccaggag gaccctgagg tgcaattcaa ctggtacgtg | 840 |
| gacggcgtcg aggtgcacaa cgccaagacc aagccccggg aggagcagtt caacagcacc | 900 |
| taccgggtcg tgtccgtgct gaccgtgctg caccaggatt ggctcaacgg caaggagtac | 960 |
| aagtgcaaag tgtccaataa gggcctgccc tcctccatcg agaagaccat ctccaaggcc | 1020 |
| aagggacaac cccgtgagcc ccaggtgtac accctgcctc cttcccagga ggagatgacc | 1080 |
| aagaatcagg tgtccctcac ctgcctggtg aagggcttct acccttccga catcgccgtg | 1140 |
| gaatgggagt ccaacggcca gcccgagaac aactacaaga caaccccccc tgtcctggac | 1200 |
| agcgacggct ccttctttct gtacagcagg ctgaccgtgg acaagagccg gtggcaggag | 1260 |
| ggcaacgtgt ttagctgtag cgtcatgcac gaggccctgc acaaccacta cacccagaaa | 1320 |

```
tccctgtccc tgtccctggg caagtgatga                                    1350
```

<210> SEQ ID NO 33
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 33

```
caggtgcagc tggtgcagtc tggggctgag gtgaagaagc ctggggcctc agtgaaggtt      60
tcctgcaagg catctggata caccttcacc gctcagtata tgcactgggt gcgacaggcc     120
cctggacaag ggcttgagtg gatgggaata atcaaccctg tggtggtga cagggtac       180 gcacagaagt tccagggcag agtcaccatg accaggaca cgtccacgag cacagtctac     240
atggagctga gcagcctgag atctgaggac acggcggtgt actactgcgc caaagaggga   300
gtggccgacg gatatggatt ggtagacgta tggggtcagg gtacaatggt caccgtctcc   360
tcagccagca ccaagggacc ctccgtgttc cctctggctc cttgcagcag gtccaccagc   420
gaatccaccg ctgccctggg ctgtctggtg aaagactact tcccgagcc tgtgaccgtg     480 agctggaact ccggcgctct gaccagcggc gtgcacacat tcctgccgt gctgcagagc     540 tccggcctgt actccctgtc ctccgtggtg acagtcccca gcagcagcct gggaaccaag   600
acctacacct gcaacgtcga ccacaagcct tccaacacca aggtggacaa gagggtggag   660
tccaaatatg gccccccctg ccctccttgt cccgctcctg agttcctggg cggcccttcc   720
gtgttcctgt tcctcccaa gcccaaggac accctgatga tctcccggac ccccgaggtg   780
acctgtgtgg tggtggacgt gtcccaggag accctgagg tgcaattcaa ctggtacgtg   840
gacggcgtcg aggtgcacaa cgccaagacc aagccccggg aggagcagtt caacagcacc   900
taccgggtcg tgtccgtgct gaccgtgctg caccaggatt ggctcaacgg caaggagtac   960
aagtgcaaag tgtccaataa gggcctgccc tcctccatcg agaagaccat ctccaaggcc  1020
aagggacaac cccgtgagcc ccaggtgtac accctgcctc cttcccagga ggagatgacc  1080
aagaatcagg tgtccctcac ctgcctggtg aagggcttct accttccga catcgccgtg  1140 gaatgggagt ccaacggcca gcccgagaac aactacaaga caacccccc tgtcctggac  1200 agcgacggct ccttctttct gtacagcagg ctgaccgtgg acaagagccg gtggcaggag  1260
ggcaacgtgt ttagctgtag cgtcatgcac gaggccctgc acaaccacta cacccagaaa  1320
tccctgtccc tgtccctggg caagtgatga                                    1350
```

<210> SEQ ID NO 34
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 34

```
caggtgcagc tggtgcagtc tggggctgag gtgaagaagc ctggggcctc agtgaaggtt      60
tcctgcaagg catctggata caccttcgag aagtactata tgcactgggt gcgacaggcc     120
cctggacaag ggcttgagtg gatgggaata atcaaccctg atggtggtag cacagggtac     180
gcacagaagt tccagggcag agtcaccatg accaggaca cgtccacgag cacagtctac     240
atggagctga gcagcctgag atctgaggac acggcggtgt actactgcgc caaagaggga   300
```

```
gtggccgacg gatatggatt ggtagacgta tggggtcagg gtacaatggt caccgtctcc      360
tcagccagca ccaagggacc ctccgtgttc cctctggctc cttgcagcag gtccaccagc      420
gaatccaccg ctgccctggg ctgtctggtg aaagactact ttcccgagcc tgtgaccgtg      480
agctggaact ccggcgctct gaccagcggc gtgcacacat tcctgccgt gctgcagagc       540 tccggcctgt actccctgtc ctccgtggtg acagtcccca gcagcagcct gggaaccaag      600
acctacacct gcaacgtcga ccacaagcct tccaacacca aggtggacaa gagggtggag      660
tccaaatatg gccccccctg ccctccttgt cccgctcctg agttcctggg cggcccttcc      720
gtgttcctgt ccctcccaa gcccaaggac accctgatga tctcccggac ccccgaggtg       780
acctgtgtgg tggtggacgt gtcccaggag gaccctgagg tgcaattcaa ctggtacgtg      840
gacggcgtcg aggtgcacaa cgccaagacc aagccccggg aggagcagtt caacagcacc      900 tacccgggtcg tgtccgtgct gaccgtgctg caccaggatt ggctcaacgg caaggagtac    960
aagtgcaaag tgtccaataa gggcctgccc tcctccatcg agaagaccat ctccaaggcc     1020
aagggacaac cccgtgagcc ccaggtgtac accctgcctc cttcccagga ggagatgacc     1080
aagaatcagg tgtccctcac ctgcctggtg aagggcttct acccttccga catcgccgtg     1140
gaatgggagt ccaacggcca gcccgagaac aactacaaga caacccccccc tgtcctggac   1200 agcgacggct ccttctttct gtacagcagg ctgaccgtgg acaagagccg gtggcaggag    1260
ggcaacgtgt ttagctgtag cgtcatgcac gaggccctgc acaaccacta cacccagaaa    1320
tccctgtccc tgtccctggg caagtgatga                                     1350
```

<210> SEQ ID NO 35
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 35

```
caggtgcagc tggtgcagtc tggggctgag gtgaagaagc ctggggcctc agtgaaggtt      60
tcctgcaagg catctggata caccttcacc agcaattata tgcactgggt gcgacaggcc    120
cctggacaag gcttgagtg gatgggaata atcaacccta gtgagggtag cacaggttac     180
gcacagaagt tccagggcag agtcaccatg accagggaca cgtccacgag cacagtctac    240
atggagctga gcagcctgag atctgaggac acggcggtgt actactgcgc caaagaggga    300
gtggccgacg gatatggatt ggtagacgta tggggtcagg gtacaatggt caccgtctcc    360
tcagccagca ccaagggacc ctccgtgttc cctctggctc cttgcagcag gtccaccagc    420
gaatccaccg ctgccctggg ctgtctggtg aaagactact ttcccgagcc tgtgaccgtg    480
agctggaact ccggcgctct gaccagcggc gtgcacacat tcctgccgt gctgcagagc     540 tccggcctgt actccctgtc ctccgtggtg acagtcccca gcagcagcct gggaaccaag    600
acctacacct gcaacgtcga ccacaagcct tccaacacca aggtggacaa gagggtggag    660
tccaaatatg gccccccctg ccctccttgt cccgctcctg agttcctggg cggcccttcc    720
gtgttcctgt ccctcccaa gcccaaggac accctgatga tctcccggac ccccgaggtg    780
acctgtgtgg tggtggacgt gtcccaggag gaccctgagg tgcaattcaa ctggtacgtg    840
gacggcgtcg aggtgcacaa cgccaagacc aagccccggg aggagcagtt caacagcacc    900 tacccgggtcg tgtccgtgct gaccgtgctg caccaggatt ggctcaacgg caaggagtac  960
aagtgcaaag tgtccaataa gggcctgccc tcctccatcg agaagaccat ctccaaggcc   1020
```

| | |
|---|---|
| aagggacaac cccgtgagcc ccaggtgtac accctgcctc cttcccagga ggagatgacc | 1080 |
| aagaatcagg tgtccctcac ctgcctggtg aagggcttct accttccga catcgccgtg | 1140 |
| gaatgggagt ccaacggcca gcccgagaac aactacaaga caaccccccc tgtcctggac | 1200 |
| agcgacggct ccttctttct gtacagcagg ctgaccgtgg acaagagccg gtggcaggag | 1260 |
| ggcaacgtgt ttagctgtag cgtcatgcac gaggccctgc acaaccacta cacccagaaa | 1320 |
| tccctgtccc tgtccctggg caagtgatga | 1350 |

<210> SEQ ID NO 36
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 36

| | |
|---|---|
| caggtgcagc tggtgcagtc tggggctgag gtgaagaagc ctggggcctc agtgaaggtt | 60 |
| tcctgcaagg catctggata caccttcagt gcgtactata tgcactgggt gcgacaggcc | 120 |
| cctggacaag gccttgagtg gatgggaata atcaaccctg atggtggtag cacagggtac | 180 |
| gcacagaagt tccagggcag agtcaccatg accagggaca cgtccacgag cacagtctac | 240 |
| atggagctga gcagcctgag atctgaggac acggcggtgt actactgcgc aaagaggga | 300 |
| gtggccgacg gatatggatt ggtagacgta tggggtcagg gtacaatggt caccgtctcc | 360 |
| tcagccagca ccaagggacc ctccgtgttc cctctggctc cttgcagcag gtccaccagc | 420 |
| gaatccaccg ctgccctggg ctgtctggtg aaagactact tccccgagcc tgtgaccgtg | 480 |
| agctggaact ccggcgctct gaccagcggc gtgcacacat tcctgccgt gctgcagagc | 540 |
| tccggcctgt actccctgtc ctccgtggtg acagtcccca gcagcagcct gggaaccaag | 600 |
| acctacacct gcaacgtcga ccacaagcct tccaacacca aggtggacaa gagggtggag | 660 |
| tccaaatatg gccccccctg ccctccttgt cccgctcctg agttcctggg cggcccttcc | 720 |
| gtgttcctgt tccctcccaa gcccaaggac accctgatga tctcccggac ccccgaggtg | 780 |
| acctgtgtgg tggtggacgt gtcccaggag gaccctgagg tgcaattcaa ctggtacgtg | 840 |
| gacggcgtcg aggtgcacaa cgccaagacc aagccccggg aggagcagtt caacagcacc | 900 |
| taccgggtcg tgtccgtgct gaccgtgctg caccaggatt ggctcaacgg caaggagtac | 960 |
| aagtgcaaag tgtccaataa gggcctgccc tcctccatcg agaagaccat ctccaaggcc | 1020 |
| aagggacaac cccgtgagcc ccaggtgtac accctgcctc cttcccagga ggagatgacc | 1080 |
| aagaatcagg tgtccctcac ctgcctggtg aagggcttct accttccga catcgccgtg | 1140 |
| gaatgggagt ccaacggcca gcccgagaac aactacaaga caaccccccc tgtcctggac | 1200 |
| agcgacggct ccttctttct gtacagcagg ctgaccgtgg acaagagccg gtggcaggag | 1260 |
| ggcaacgtgt ttagctgtag cgtcatgcac gaggccctgc acaaccacta cacccagaaa | 1320 |
| tccctgtccc tgtccctggg caagtgatga | 1350 |

<210> SEQ ID NO 37
<211> LENGTH: 648
<212> TYPE: DNA
<213> ORGANISM: Artificial Sequence
<220> FEATURE:
<223> OTHER INFORMATION: Synthetic Construct

<400> SEQUENCE: 37

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaaa gggccactgg catcccagcc     180
aggttcagtg gcagtgggtc tgggacagac ttcactctca ccatcagcag cctagagcct     240
gaagattttg cagtttatta ctgtgaccag agaaacaatt ggcctctcac ttttggcgga     300
gggaccaagg ttgagatcaa acggaccgtg gctgccccta gcgtgttcat cttccctccc     360
tccgatgagc agctcaagtc cggcacagcc agcgtggtgt gcctgctgaa taacttctac     420 cccggagg ccaaagtgca gtggaaggtg gacaacgctc tgcagtccgg caattcccag     480
gagagcgtca ccgagcagga cagcaaggac agcacctact ccctgagctc caccctgacc     540
ctgagcaagg ccgactacga aagcacaag gtctacgcct gcgaggtcac ccatcagggc     600
ctgtccagcc ccgtgaccaa gtccttcaac cggggcgagt gctgatga                648
```

<210> SEQ ID NO 38
<211> LENGTH: 288
<212> TYPE: PRT
<213> ORGANISM: Mus musculus

<400> SEQUENCE: 38

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255
```

```
Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285
```